US012760332B2

(12) United States Patent
Redding et al.

(10) Patent No.: US 12,760,332 B2
(45) Date of Patent: Oct. 13, 2026

(54) PHOTOSYSTEM I-BACTERIAL HYDROGENASE CHIMERAS FOR HYDROGEN PRODUCTION

(71) Applicant: ARIZONA BOARD OF REGENTS ON BEHALF OF ARIZONA STATE UNIVERSITY, Scottsdale, AZ (US)

(72) Inventors: Kevin Redding, Tempe, AZ (US); Andrey Kanygin, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 445 days.

(21) Appl. No.: 18/349,764

(22) Filed: Jul. 10, 2023

(65) Prior Publication Data

US 2024/0093246 A1 Mar. 21, 2024

Related U.S. Application Data

(60) Provisional application No. 63/359,666, filed on Jul. 8, 2022.

(51) Int. Cl.

| | |
|---|---|
| ***C12P 3/00*** | (2006.01) |
| ***C07K 14/405*** | (2006.01) |
| ***C12N 9/02*** | (2006.01) |
| ***C12N 15/62*** | (2006.01) |

(52) U.S. Cl.

CPC .............. *C12P 3/00* (2013.01); *C07K 14/405* (2013.01); *C12N 9/0067* (2013.01); *C12N 15/62* (2013.01); *C12Y 112/07002* (2013.01); *C07K 2319/00* (2013.01)

(58) Field of Classification Search

CPC .. C07K 14/405; C12N 15/62; C12N 2510/00; C12N 5/10

See application file for complete search history.

(56) References Cited

U.S. PATENT DOCUMENTS

| | | | |
|---|---|---|---|
| 7,396,664 | B2 | 7/2008 | Daly et al. |
| 7,501,270 | B2 | 3/2009 | King et al. |
| 2022/0204996 | A1 | 6/2022 | Redding et al. |

OTHER PUBLICATIONS

Ben-Shem et al. Nature, 2003, 436, 630-635 (Year: 2003).*
Ihara et al. Photochem. & Photobiol., 2006, 82, 676-682 (Year: 2006).*
Fischer et al. Biochemistry, 1997, 36, 93-102 (Year: 1997).*
Bingham et al. Int. J. Hydrogen Energy, 2012, 37, 2965-2976 (Year: 2012).*
Happe and Kaminski Eur. J. Biochem., 2002, 269, 1022-1032 (Year: 2002).*
Betts and Russell Bioinformatics for Geneticists, 2003, chapter 14, 289-316 (Year: 2003).*
Kanygin et al. Energy Environ. Sci., 2020, 13, 2903-2914 (Year: 2020).*
Kanygin et al. Energy Environ. Sci., 2020, 13, Suppl. Material (Year: 2020).*
Caserta et al. J. Am. Chem. Soc., 2018, 140, 5516-5526 (Year: 2018).*
Caserta et al. J. Am. Chem. Soc., 2018, 140, Suppl. Information (Year: 2018).*
Winkler et al. Nature Commun., 2021, (Year: 2021).*
Altschul et al., 1997, Nucl. Acids Res. 25: 3389-3402.
Atta M, Meyer J. Characterization of the gene encoding the [Fe]-hydrogenase from Megasphaera elsdenii. Biochim Biophys Acta—Protein Struct Mol Enzymol 2000; 1476:368-71. https://doi.org/10.1016/S0167-4838(99)00245-9.
Brettel K. Electron transfer and arrangement of the redox cofactors in photosystem I. Biochim Biophys Acta—Bioenerg 1997;1318:322-73. https://doi.org/10.1016/S0005-2728(96)00112-0.
Caserta G, Papini C, Adamska-Venkatesh A, Pecqueur L, Sommer C, Reijerse E, et al. Engineering an [FeFe]-Hydrogenase: Do Accessory Clusters Influence O 2 Resistance and Catalytic Bias? J Am Chem Soc 2018;140:5516-26. https://doi.org/10.1021/jacs.8b01689.
Chaux F, Burlacot A, Mekhalfi M, Auroy P, Blangy S, Richaud P, et al. Flavodiiron Proteins Promote Fast and Transient O2 Photoreduction in Chlamydomonas. Plant Physiol 2017; 174:1825 LP-1836. https://doi.org/10.1104/ pp. 17.00421.
Cournac L, Mus F, Bernard L, Guedeney G, Vignais PM, Peltier G. Limiting steps of hydrogen production in Chlamydomonas reinhardtii and Synechocystis PCC 6803 as analysed by light-induced gas exchange transients. Int J Hydrogen Energy 2002;27:1229-37. https://doi.org/10.1016/S0360-3199(02)00105-2.
Dang K-V, Plet J, Tolleter D, Jokel M, Cuiné S, Carrier P, et al. Combined Increases in Mitochondrial Cooperation and Oxygen Photoreduction Compensate for Deficiency in Cyclic Electron Flow in Chlamydomonas reinhardtii. Plant Cell 2014;26:3036-50. https://doi.org/10.1105/tpc.114.126375.
Elman T, Hoai Ho TT, Milrad Y, Hippler M, Yacoby I. Enhanced chloroplast-mitochondria crosstalk promotes ambient algal-H2 production. Cell Reports Phys Sci 2022;3:100828. https://doi.org/10.1016/j.xcrp.2022.100828.
Engelbrecht V, Liedtke K, Rutz A, Yadav S, Günzel A, Happe T. One isoform for one task? The second hydrogenase of Chlamydomonas reinhardtii prefers hydrogen uptake. Int J Hydrogen Energy 2021;46:7165-75. https://doi.org/10.1016/j.ijhydene.2020.11.231.
Eroglu E, Melis A. Microalgal hydrogen production research. Int J Hydrogen Energy 2016;41:12772-98. https://doi.org/ https://doi.org/10.1016/j.ijhydene.2016.05.115.
Fischer N, Sétif P, Rochaix JD. Targeted Mutations in the psaC Gene of Chlamydomonas reinhardtii: Preferential Reduction of FB at Low Temperature Is Not Accompanied by Altered Electron Flow from Photosystem I to Ferredoxin. Biochemistry 1997;36:93-102. https://doi.org/10.1021/bi962244v.

(Continued)

*Primary Examiner* — Sharmila G Landau
*Assistant Examiner* — Lioubov G Korotchkina
(74) *Attorney, Agent, or Firm* — Quarles & Brady LLP

(57) ABSTRACT

Provided herein, in some embodiments, are engineered cells and use of the same for increased hydrogen production. In particular, provided herein are genetically engineered cells comprising a polynucleotide encoding a fusion protein comprising a photosystem I (PSI) protein and a bacterial hydrogenase, as well as methods for producing such genetically engineered cells. Also provided herein are methods for increasing hydrogen ($H_2$) production in cells.

4 Claims, 16 Drawing Sheets

Specification includes a Sequence Listing.

(56) References Cited

OTHER PUBLICATIONS

Gerde JA, Montalbo-Lomboy M, Yao L, Grewell D, Wang T. Evaluation of microalgae cell disruption by ultrasonic treatment. Bioresour Technol 2012;125:175-81. https://doi.org/10.1016/j.biortech.2012.08.110.
Ghirardi ML, Togasaki RK, Seibert M. Oxygen sensitivity of algal H2-production. Appl Biochem Biotechnol 1997;67:182. https://doi.org/10.1007/BF02787851.
Gulis G, Narasimhulu K V, Fox LN, Redding KE. Purification of His6-tagged Photosystem I from Chlamydomonas reinhardtii. Photosynth Res 2008;96:51-60. https://doi.org/10.1007/s11120-007-9283-9.
Hohmann-Marriott MF, Blankenship RE. Evolution of Photosynthesis. Annu Rev Plant Biol 2011;62:515-48. https://doi.org/10.1146/annurev-arplant-042110-103811.
Hwang J-H, Lee WH. Continuous photosynthetic biohydrogen production from acetate-rich wastewater: Influence of light intensity. Int J Hydrogen Energy 2021;46:21812-21. https://doi.org/10.1016/j.ijhydene.2021.04.052.
Kanygin A, Milrad Y, Thummala C, Reifschneider K, Baker P, Marco P, et al. Rewiring photosynthesis: a photosystem I-hydrogenase chimera that makes H2 in vivo. Energy Environ Sci 2020; 13:2903-14. https://doi.org/10.1039/C9EE03859K.
Kanygin A, Smith A, Nagy V, Tóth SZ, Redding KE. Interplay between Hydrogen Production and Photosynthesis in a Green Alga Expressing an Active Photosystem I-hydrogenase Chimera. Int J Hydrogen Energy 2022; (accepted for publication on Mar. 11, 2022).
Kanygin, "Engineering the next-generation type I reaction centers specializing in H2 production in vivo," A Dissertation, Aug. 2022.
Karlin and Altschul, 1990, Proc. Natl. Acad. Sci. USA 87: 2267-2268.
Kelley LA, Mezulis S, Yates CM, Wass MN, Sternberg MJE. The Phyre2 web portal for protein modeling, prediction and analysis. Nat Protoc 2015; 10:845-58. https://doi.org/10.1038/nprot.2015.053.
Kozakov D, Hall DR, Xia B, Porter KA, Padhorny D, Yueh C, et al. The ClusPro web server for protein-protein docking. Nat Protoc 2017;12:255. https://doi.org/10.1038/nprot.2016.169.
Kozuleva M, Petrova A, Milrad Y, Semenov A, Ivanov B, Redding KE, et al. Phylloquinone is the principal Mehler reaction site within photosystem I in high light. Plant Physiol 2021; 186:1848-58. https://doi.org/10.1093/plphys/kiab221.
Kropat J, Hong-Hermesdorf A, Casero D, Ent P, Castruita M, Pellegrini M, et al. A revised mineral nutrient supplement increases biomass and growth rate in Chlamydomonas reinhardtii. Plant J 2011;66:770-80. https://doi.org/10.1111/j.1365-313X.2011.04537.x.
Lubitz W, Ogata H, Rüdiger O, Reijerse E. Hydrogenases. Chem Rev 2014;114:4081-148. https://doi.org/10.1021/cr4005814.
Milrad Y, Schweitzer S, Feldman Y, Yacoby I. Bi-directional electron transfer between H2 and NADPH mitigates light fluctuation responses in green algae. Plant Physiol 2021; 186:168-79. https://doi.org/10.1093/plphys/kiab051.
Milrad Y, Schweitzer S, Feldman Y, Yacoby I. Green Algal Hydrogenase Activity Is Outcompeted by Carbon Fixation before Inactivation by Oxygen Takes Place. Plant Physiol 2018;177:918-26. https://doi.org/10.1104/ pp. 18.00229.
Mühlenhoff U, Sétif P. Laser Flash Absorption Spectroscopy Study of Flavodoxin Reduction by Photosystem I in *Synechococcus* sp. PCC 7002. Biochemistry 1996;35:1367-74. https://doi.org/10.1021/bi952381c.
Nagy V, Podmaniczki A, Vidal-Meireles A, Tengölics R, Kovács L, Rákhely G, et al. Water-splitting-based, sustainable and efficient H2 production in green algae as achieved by substrate limitation of the Calvin-Benson-Bassham cycle. Biotechnol Biofuels 2018;11:69. https://doi.org/10.1186/s13068-018-1069-0.
Nawrocki WJ, Bailleul B, Picot D, Cardol P, Rappaport F, Wollman F-A, et al. The mechanism of cyclic electron flow. Biochim Biophys Acta—Bioenerg 2019;1860:433-8. https://doi.org/10.1016/j.bbabio.2018.12.005.
Nelson N, Ben-Shem A. The complex architecture of oxygenic photosynthesis. Nat Rev Mol Cell Biol 2004;5:971.
Nelson N, Junge W. Structure and Energy Transfer in Photosystems of Oxygenic Photosynthesis. Annu Rev Biochem 2015;84:659-83. https://doi.org/10.1146/annurev-biochem-092914-041942.
Pinto TS, Malcata FX, Arrabaça JD, Silva JM, Spreitzer RJ, Esquivel MG. Rubisco mutants of Chlamydomonas reinhardtii enhance photosynthetic hydrogen production. Appl Microbiol Biotechnol 2013;97:5635-43. https://doi.org/10.1007/s00253-013-4920-z.
Porra RJ, Thompson WA, Kriedemann PE. Determination of accurate extinction coefficients and simultaneous equations for assaying chlorophylls a and b extracted with four different solvents: verification of the concentration of chlorophyll standards by atomic absorption spectrosco. Biochim Biophys Acta—Bioenerg 1989;975:384-94. https://doi.org/10.1016/S0005-2728(89)80347-0.
Redding KE, Appel J, Boehm M, Schuhmann W, Nowaczyk MM, Yacoby I, et al. Advances and challenges in photosynthetic hydrogen production. Trends Biotechnol 2022. https://doi.org/10.1016/j.tibtech.2022.04.007.
Reifschneider-Wegner et al. Expression of the [FeFe] hydrogenase in the chloroplast of Chlamydomonas reinhardtii. Int J of Hydrogen Energy 39: 3657-3665 (2014).
Sawyer A, Bai Y, Lu Y, Hemschemeier A, Happe T. Compartmentalisation of [FeFe]-hydrogenase maturation in Chlamydomonas reinhardtii. Plant J 2017;90:1134-43. https://doi.org/10.1111/tpj.13535.
Sétif P. Ferredoxin and flavodoxin reduction by photosystem I. Biochim Biophys Acta—Bioenerg 2001;1507:161-79. https://doi.org/https://doi.org/10.1016/S0005-2728(01)00205-5.
Sievers F, Wilm A, Dineen D, Gibson TJ, Karplus K, Li W, et al. Fast, scalable generation of high-quality protein multiple sequence alignments using Clustal Omega. Mol Syst Biol 2011;7:539. https://doi.org/10.1038/msb.2011.75.
Song Y, DiMaio F, Wang RY-R, Kim D, Miles C, Brunette T, et al. High-Resolution Comparative Modeling with RosettaCM. Structure 2013;21:1735-42. https://doi.org/10.1016/j.str.2013.08.005.
Suga M, Ozawa S-I, Yoshida-Motomura K, Akita F, Miyazaki N, Takahashi Y. Structure of the green algal photosystem I supercomplex with a decameric light-harvesting complex I. Nat Plants 2019;5:626-36. https://doi.org/10.1038/s41477-019-0438-4.
Sun Y, Chen M, Yang H, Zhang J, Kuang T, Huang F. Enhanced H2 photoproduction by down-regulation of ferredoxin-NADP+ reductase (FNR) in the green alga *Chlamydomonas reinhardtii*. Int J Hydrogen Energy 2013;38:16029-37. https://doi.org/10.1016/J.IJHYDENE.2013.10.011.
Suslick KS. Sonochemistry. Science (80-) 1990;247:1439-45. https://doi.org/10.1126/science.247.4949.1439.
Swanson KD, Ratzloff MW, Mulder DW, Artz JH, Ghose S, Hoffman A, et al. [FeFe]-Hydrogenase Oxygen Inactivation Is Initiated at the H Cluster 2Fe Subcluster. J Am Chem Soc 2015;137:1809-16. https://doi.org/10.1021/ja510169s.
Torzillo G, Scoma A, Faraloni C, Giannelli L. Advances in the biotechnology of hydrogen production with the microalga *Chlamydomonas reinhardtii*. Crit Rev Biotechnol 2015;35:485-96. https://doi.org/10.3109/07388551.2014.900734.
Vassiliev IR, Jung Y-S, Yang F, Golbeck JH. PsaC Subunit of Photosystem I Is Oriented with Iron-Sulfur Cluster FB as the Immediate Electron Donor to Ferredoxin and Flavodoxin. Biophys J 1998;74:2029-35. https://doi.org/10.1016/S0006-3495(98)77909-3.

* cited by examiner

FIG. 2

```
                    β-hairpin
                      |    |
MAHIVKIYDTCIGCTQCVRACPLDVLEMVPWDGCKASQMASAPRTEDCVGCKRCETACPT  60 #1
MSHTVKIYDTCIGCTQCVRACPTDVLEMVPWDGCKASQIASAPRTEDCVGCKRCESACPT  60 #2
MSHTVKIYDTCIGCTQCVRACPTDVLEMVPWNGCKANQIASAPRTEDCVGCKRCESACPT  60 #3
MAHTVKIYDNCIGCTQCVRACPLDVLEMVPWDGCKAGQMASAPRTEDCVGCKRCETACPT  60 #4
*.*:*****:************.********:****.*:****************.****

DFLSVRVYLGSESTRSMGLSY  81 #1
DFLSVRVYLGSETTRSMGLAY  81 #2
DFLSVRVYLGAETTRSMGLAY  81 #3
DFLSIRVYLGGETTRSMGLAY  81 #4
****:*****.*:******:*
```

FIG. 3

SEQ ID NO: 1

MAHIVKIYDTCIGCTQCVRACPLDVLEMVPWGGATATDAVPNDVDKVKA
ALKDPEKIVIFQTAPAVRVGLGEAFGMDPGTFVEGKMVAALRTLGADYV
FDTDFGADLTIMEEATELLHRLQSEEIPIPQFTSCCPAWVEFAETFYPDLL
QHLSSTKSPISILSPVIKTYFAQQKNIDPKKIVNVCVTPCTAKKAEIRRPEL
SASGLFWDEPEIRDTDICITTRELAQWIQDENIDFASLEDSKFDKAFGEA
SGGGRIFGNSGGVMEAAIRTAYHMFTGRPAPKDFIPFEPVRGLQGVKK
ATVIFGHFVLHVAAISGLGNARAFIDDLIKNDAFEDYSFIEVMACPGGCIG
GGGQPKVKLPQVKKVQEARTASIYKSDEETDIKASWQNPEIETLYEAFL
DEPLSEMAEFTLHTHYSAGSGGGGSGAGGASQMASAPRTEDCVGCK
RCETACPTDFLSVRVYLGSESTRSMGLSY

FIG. 4

```
MeHydA   MPEFHSRFEKIDRRVPIDEHNCAVQFDVTKCKNCTLCRRACADTQTVLDYYSLSSTGDMP   60
HydA1    ------------------------------------------------------------   0
HydA2    ------------------------------------------------------------   0

MeHydA   ICVHCGQCSSACPFGA-IVEVNDVDKVKAALKDPEKIVIFQTAPAVRVGLGEAFGMDPGT   119
HydA1    -----AAPAAEAPLSHVQQALAELAK--PKDDPTRKHVCVQVAPAVRVAIAETLGLAPGA   53
HydA2    --------TATDAVPHWKLALEELDK--PKDG-GRKVLIAQVAPAVRVAIAESFGLAPGA   49
                  ::    .       : :: *         .* :  *.******.:.*::*: **:

MeHydA   FVEGKMVAALRTLGADYVFDTDFGADLTIMEEATELLHRLQS-------EEIPIPQFTSC   172
HydA1    TTPKQLAEGLRRLGFDEVFDTLFGADLTIMEEGSELLHRLTEHLEAHPHSDEPLPMFTSC   113
HydA2    VSPGKLAAGLRALGFDQVFDTLFAADLTIMEEGTELLHRLKEHLEAHPHSDEPLPMFTSC   109
             ::. .** ** * **** *.********.:****** .       .: *:* ****

MeHydA   CPAWVEFAETFYPDLLQHLSSTKSPISILSPVIKTYFAQQKNIDPKKIVNVCVTPCTAKK   232
HydA1    CPGWIAMLEKSYPDLIPYVSSCKSPQMMLAAMVKSYLAEKKGIAPKDMVMVSIMPCTRKQ   173
HydA2    CPGWVAMMEKSYPELIPFVSSCKSPQMMMGAMVKTYLSEKQGIPAKDIVMVSVMPCVRKQ   169
         **.*: : *. **:*: .:** ***   ::. ::*:*::::.*  *.:* *.: **. *:

MeHydA   AEIRRPELSASGLFWDEPEIRDTDICITTRELAQWIQDENIDFASLEDSKFDKAFGEASG   292
HydA1    SEADRDWFCV----DADPTLRQLDHVITTVELGNIFKERGINLAELPEGEWDNPMGVGSG   229
HydA2    GEADREWFCV----S-EPGVRDVDHVITTAELGNIFKERGIILPELPDSDWDQPLGLGSG   224
         .*  *  :..        :* :*: *  *** **.: :::..* : .* :..:*: :* .**

MeHydA   GGRIFGNSGGVMEAAIRTAYHMFTGRPAPKDFIPFEPVRGLQGVKKATVIF---------   343
HydA1    AGVLFGTTGGVMEAALRTAYELFTGTPLPRL--SLSEVRGMDGIKETNITMVPAPGSKFE   287
HydA2    AGVLFGTTGGVMEAAVRTAYEIVTKEPLPRL--NLSEVRGLDGIKEASVTLVPAPGSKFA   282
         .* :**.:*******:****.:.*  * *:     :. ***::*:*::.: :

MeHydA   ---------------------------------------------GMFVLMVAAISGLGN   358
HydA1    ELLKHRAAARAEAA---------AHGTPGPLAWDGGAGFTSEDGRGGITLRVAVANGLGN   338
HydA2    ELVAARLAHKVEEAAAAEAAAAVEGAVKPPIAYDGGQGFSTDDGKGGLKLRVAVANGLGN   342
                                                      * : *:**. .****

MeHydA   ARAFIDDLIKNDAFEDYSFIEVMACPGGCIGGGGQPKVKLPQVKKVQEARTASIYKSDEE   418
HydA1    AKKLITKMQAGE--AKYDFVEIMACPAGCVGGGGQPRSTDK---AITQKRQAALYNLDEK   393
HydA2    AKKLIGKMVSGE--AKYDFVEIMACPAGCVGGGGQPRSTDK---QITQKRQAALYDLDER   397
         *: :* .: .:    .*.*:*:****.**:******: .        : : * *::*. **.

MeHydA   TDIKASWQNPEIETLYEAFLDEPLSEMAEFTLHTYFSDKSDQLGRMKNLTPQTNPMSPKY   478
HydA1    STLRRSHENPSIRELYDTYLGEPLGHKAHELLHTHYVAGGVEEKDEKK------------   441
HydA2    NTLRRSHENEAVNQLYKEFLGEPLSHRAHELLHTHYVPGGAEADA---------------   442
         . :: * :*  :. **. :*.***.. *.  **::   . :

MeHydA   KPPTEE   484
HydA1    ------   441
HydA2    ------   442
```

FIG. 7

```
PsaCMeHydA          MAHIVKIYDTCIGCTQCVRACPLDVLEMVPW[redacted]NDVDKVKAA----LKDPEK  56
PsaCMeHydA_null     MAHIVKIYDTCIGCTQCVRACPLDVLEMVPW[redacted]NDVDKVKAA----LKDPEK  53
PsaCHydA2           MAHIVKIYDTCIGCTQCVRACPLDVLEMVPW[redacted]HWKLALEELDKPRDGG-RK  59
PsaCHydA1           MAHIVKIYDTCIGCTQCVRACPLDVLEMVPW[redacted]HVQQALAELAKPKDDPTRK  60
                    *******************************  .     :    :           .*

PsaCMeHydA          IVIFQTAPAVRVGLGEAFGMDPGTFVEGRMVAALRTLGADYVFDTDFGADLTIMEEATEL  116
PsaCMeHydA_null     IVIFQTAPAVRVGLGEAFGMDPGTFVEGRMVAALRTLGADYVFDTDFGADLTIMEEATEL  113
PsaCHydA2           VLIAQVAPAVRVAIAESFGLAPGAVSPGKLATGLRALGFDQVFDTLFAADLTIMEEGTEL  119
PsaCHydA1           HVCVQVAPAVRVAIAETLGLAPGATTPKQLAEGLRRLGFDEVFDTLFGADLTIMEEGSEL  120
                      :   *.******.:.*::*: **:      ::. .** ** * **** *.********.:**

PsaCMeHydA          LHRLQS-------EEIFIPQFTSCCPAWVEFAETFYPDLLQHLSSTKSPISILSPVIKTY  169
PsaCMeHydA_null     LHRLQS-------EEIFIPQFTSCCPAWVEFAETFYPDLLQHLSSTKSPISILSPVIKTY  166
PsaCHydA2           LHRLKEHLEAHPHSDEPLPMFTSCCPGWVAMMEKSYPELIPFVSSCKSPQMMMGAMVKTY  179
PsaCHydA1           LHRLTEHLEAHPHSDEPLPMFTSCCPGWIAMLEKSYPDLIPYVSSCKSPQMMLAAMVKSY  190
                    ****  .         .: *:* ******.*: : *. **:*: .:** ***   ::. ::*:*

PsaCMeHydA          FAQQKNIDPKKIVNVCVTPCTAKKAEIRRPELSASGLFWDEPEIRDTDICITTRELAQWI  229
PsaCMeHydA_null     FAQQKNIDPKKIVNVCVTPCTAKKAEIRRPELSASGLFWDEPEIRDTDICITTRELAQWI  226
PsaCHydA2           LSEKQGIPAKDIVMVSVMPCVRKQSEADREWPCV-----S-EPGVRDVDHVITTAELGNIF  234
PsaCHydA1           LAEKKGIAPKDMVMVSIMPCTRKQSEADRDWPCV----DADPTLRQLDHVITTVELGNIF  236
                    :::::.*  *.:* *.: **. *:.*  *  :..        :* :*: *  *** **.: :

PsaCMeHydA          QDENIDFASLEDSKFDKAFGEASGGGRIFGNSGGVMEAAIRTAYHMFTGRPAPKDFIPFE  289
PsaCMeHydA_null     QDENIDFASLEDSKFDKAFGEASGGGRIFGNSGGVMEAAIRTAYHMFTGRPAPKDFIPFE  286
PsaCHydA2           KERGINLPELPDSDWDQPLGLGSGAGVLFGTTGGVMEAALRTAYEIVTKEPLPRL--NLS  292
PsaCHydA1           KERGINLAELPEGEWDNPMGVGSGAGVLFGTTGGVMEAALRTAYELFTGTPLPRL--SLS  294
                    ::..*:: .* :..:*: :* .**.* :**.:*******:****.:.*  * *:       :.

PsaCMeHydA          FVRGLQGVKKATVIF-------------------------------------------  304
PsaCMeHydA_null     FVRGLQGVKKATVIF-------------------------------------------  301
PsaCHydA2           EVRGLDGIKEASVTLVPAPGSKFAELVAERLAHKVEEAAAAEAAAAVEGAVRPPIAYDGG  352
PsaCHydA1           EVRGMDGIKETNITMVPAPGSKFEELLKHRAAAARAEAA---------AHGTPGPLAWDGG  345
                     ***::*:*::.: :

PsaCMeHydA          ---------GHFVLHVAAISGLGNAKAFIDDLIKNDAPEDYSFIEVMACPGGCIGGGGQP  355
PsaCMeHydA_null     ---------GHFVLHVAAISGLGNAKAFIDDLIKNDAPEDYSFIEVMACPGGCIGGGGQP  352
PsaCHydA2           QGFSTDDGKGGLKLRVAVANGLGNAKKLIGRMVSGE--AKYDFVEIMACPAGCVGGGGQP  410
PsaCHydA1           AGFTSEDGRGGITLKVAVANGLGNAKKLITRMQAGE--AKYDFVEIMACPAGCVGGGGQP  403
                              * : *:**. .*****: :* .:  .:    .*.*:*:****.**:******

PsaCMeHydA          KVKLPQVRKVQEARTASIYKSDEETDIKASWQNPEIETLYEAFLDEPLSEMAEFTLHT[redacted]  415
PsaCMeHydA_null     KVKLPQVRKVQEARTASIYKSDEETDIKASWQNPEIETLYEAFLDEPLSEMAEFTLHT[redacted]  412
PsaCHydA2           RSTDK---QITQKRQAALYDLDERNTLRRSHENEAVNQLYKEFLGEPLSHRAHELLHT[redacted]  467
PsaCHydA1           RSTDK---AITQKRQAALYNLDEKSTLRRSHENPSIRELYDTYLGEPLGHKAHELLHT[redacted]  460
                    : .       : :  * *::*. **.. :: * :*  :. **. :*.***.. *.   ***::

PsaCMeHydA          [redacted]ASQMASAPRTEDCVGCKRCETACPTDFLSVRVYLGSESTRSMGLSY-  474
PsaCMeHydA_null     [redacted]ASQMASAPRTEDCVGCKRCETACPTDFLSVRVYLGSESTRSMGLSY-  464
PsaCHydA2           [redacted]ASQMASAPRTEDCVGCKRCETACPTDFLSVRVYLGSESTRSMGLSY-  517
PsaCHydA1           [redacted]ASQMASAPRTEDCVGCKRCETACPTDFLSVRVYLGSESTRSMGLSY*  510
                                 ************************************************
```

PHOTOSYSTEM I-BACTERIAL HYDROGENASE CHIMERAS FOR HYDROGEN PRODUCTION

CROSS-REFERENCE TO RELATED APPLICATIONS

This application claims priority to, and the benefit of, U.S. Application No. 63/359,666 filed Jul. 8, 2022, the content of which is incorporated herein by reference in its entirety

STATEMENT REGARDING FEDERALLY SPONSORED RESEARCH OR DEVELOPMENT

This invention was made with government support under 1706960 awarded by the National Science Foundation. The government has certain rights in the invention.

SEQUENCE LISTING

This application is being filed electronically via EFS-Web and includes an informal Sequence Listing in .xml format. The contents of the electronic sequence listing (112624.01410.xml; Size: 24,842 bytes; and Date of Creation: Jul. 28, 2023) is herein incorporated by reference in its entirety.

BACKGROUND

Conversion of algal cells into solar-powered biofactories generating high-energy product molecules is a promising avenue for addressing the ever-increasing global energy demand, due to its environmental friendliness and cheap replication. Hydrogen ($H_2$) is an attractive target product for several reasons. It is an important commodity with over 60 million tons produced globally, but about 95% of it is produced from steam reformation of fossil fuels, thus contributing to the rise of atmospheric $CO_2$. The [FeFe] hydrogenase enzyme catalyzes the rapid and reversible reduction of protons ($2H^+ + 2e^- \leftrightarrows H_2$). The active site of the enzyme is a metallic cofactor that is $O_2$-sensitive and must be inserted by maturation factors.

Photosynthesis has been driving biomass accumulation on Earth for over 3 billion years, using fleeting light energy conversion into stable chemical bonds by pigment-protein machinery. As the oxygenic photosynthesis became dominant, the light could do the most work by splitting water into oxygen, protons, and reducing electrons. In the thylakoid membranes of the chloroplast, the photosynthetic electron transport chain (PETC) performs light-driven electron transport from water to ferredoxin (Fd) and pumps protons across the membrane, ultimately providing metabolic energy (ATP) and low-potential reductant (NADPH) to drive $CO_2$ fixation by the Calvin-Benson-Bassham (CBB) cycle.

Low redox potential electrons traverse energetically downhill via the PETC using energy differences to generate proton gradient. First, at acceptor side of Photosystem II the quinone is reduced to quinol taking two protons and two electrons from the stromal side and via the Q-cycle, involving cytochrome $b_6f$, releasing 4 protons (per 2 electrons transported) at the luminal side of the membrane. Then, these electrons are "reenergized" by Photosystem-I becoming highly reducing (~−520-590 mV at PSI acceptor side cofactors) and readily go to ferredoxin ($E_m^o$=−430 mV). Ferredoxins are a logistical hub for electrons in the stroma, with delivery based on the momentary needs of the cell. When electrons are delivered to ferredoxin-NADP reductase (FNR) to make NADPH, it is called linear electron flow. When electrons are delivered back to the quinone pool (via cytochrome $b_6f$), it is called cyclic electron flow (CEF). The former is used for carbon fixation resulting in NADPH and ATP consumption, while the latter allows supplementary ATP synthesis via additional proton pumping.

Alternative pathways for reductant at ferredoxin level take place when the linear pathway is stalling or cyclic electron flow is impaired. To prevent overreduction and damage to PSI, electrons can follow the path of $O_2$ reduction if $O_2$ is available: either directly via Mehler reaction or flavodiiron proteins mediated pathway. In the absence of oxygen, some microalga developed a mechanism that involves hydrogenases—metalloenzymes catalyzing reversible proton reduction, thusly, reductant changes phase from liquid to gaseous storing energy as molecular hydrogen that can be recaptured later and converted back to reduced ferredoxin.

It has been shown that some of the reducing power can be captured and redirected from carbon fixation to proton reduction, hence, changing the energy storage molecule from carbohydrate to molecular hydrogen. In that work, endogenous [FeFe] hydrogenases of *Chlamydomonas reinhardtii* have been used, which are notoriously oxygen sensitive. In the two endogenous hydrogenases, function significantly suffers from oxygen inactivation, as active oxygen removal methods improve chimeric hydrogenase activity. Without a way to keep most of the chimeric protein active, photobiological hydrogen production cannot approach its theoretical maximum of solar-to-hydrogen conversion efficiency of ~13% as electrons are diverted to alternative electron acceptors ($O_2$) and become feasible for industrial scale. A wild-type *Chlamydomonas* light-to-hydrogen energy conversion efficiency is typically an order of magnitude lower and is around 1.61% under conditions of mitigating $O_2$ by respiration. Accordingly, there remains a need in the art for improved efficient, scalable, and economically feasible methods of producing hydrogen in algae.

SUMMARY OF THE DISCLOSURE

Fusion proteins, genetically engineered cells and expression cassettes comprising polynucleotides encoding the fusion proteins are provided herein as well as methods of using the same.

In an aspect, a genetically engineered cell comprising a polynucleotide encoding a fusion protein comprising a photosystem I (PSI) protein and a bacterial hydrogenase is provided. In embodiments, the PSI protein is PsaC. In embodiments, the hydrogenase is bacterial hydrogenase A (HydA). In embodiments, the hydrogenase is inserted in frame into the PSI protein. In embodiments, the hydrogenase is inserted in frame into the hinge region of PsaC.

In embodiments, the polynucleotide further comprises a nucleic acid linker encoding at least one amino acid at the junction between the PsaC protein and the hydrogenase protein at the N-terminal end of the fusion protein, the C-terminal end of the fusion protein, or both ends of the fusion protein.

In embodiments, the polynucleotide encodes the polypeptide of SEQ ID NO: 1 or 12 or a polypeptide having 95% identity to SEQ ID NO: 1 or 12.

In embodiments, the bacterial hydrogenase is a *Megasphaera elsdenii* hydrogenase or a *Clostridium beijerincki* hydrogenase. In embodiments, the hydrogenase F-domain is removed.

In embodiments, the cell is an algal cell. In embodiments, the cell is selected from *Chlamydomonas reinhardtii, Chlorella vulgaris, Picochlorum soloecismus, Galdieria sulphuraria* and *Cyanidioschyzon merolae.*

In another aspect, provided herein is an algal biomass comprising the genetically engineered cell described herein.

In another aspect, provided herein is an expression cassette comprising a polynucleotide encoding a fusion protein comprising a PSI protein and a bacterial hydrogenase, wherein the polynucleotide is operably linked to a promoter that drives expression of the fusion protein. In embodiments, the PSI protein is PsaC. In embodiments, the polynucleotide comprises bacterial hydrogenase A inserted in frame into the β-hairpin of PsaC. In embodiments, the polynucleotide further comprises a nucleic acid linker encoding at least one amino acid at the junction between the PSA protein and the hydrogenase protein at the N-terminal end of the fusion protein, the C-terminal end of the fusion protein, or both ends of the fusion protein. In embodiments, the polynucleotide encodes the polypeptide of SEQ ID NO: 1 or 12 or a polypeptide having at least 95% identity to SEQ ID NO: 1 or 12.

In another aspect, provided herein is a method of increasing hydrogen ($H_2$) production in a cell, the method comprising (a) introducing into the cell the expression cassette described herein to produce a genetically engineered cell; and (b) culturing the genetically engineered cell under continuous illumination, wherein the genetically engineered cell exhibits at least a 4-fold increase in $H_2$ production under such conditions relative to a control cell of the same species under the same conditions.

In another aspect, provided herein is a fusion protein comprising a bacterial FeFe hydrogenase or functional portion thereof inserted into a PsaC protein. In embodiments, the fusion protein comprises SEQ ID NO: 1 or 12 or a polypeptide having at least 95% identity to SEQ ID NO: 1 or 12.

BRIEF DESCRIPTION OF THE DRAWINGS

FIG. 2 presents alignment of algal PsaC polypeptide sequences. Alignment order is #1 (SEQ ID NO: 7) PsaC_*Chlamydomonas reinhardtii,* #2 (SEQ ID NO: 8) PsaC_*Chlorella vulgaris,* #3 (SEQ ID NO: 9) PsaC_*Picochlorum soloecismus,* #4 (SEQ ID NO: 10) PsaC_*Cyanidioschyzon merolae.* Star (*) represents identical residues, colon (:) similar residues and dot (.) not similar residues. β-harpin is donated by | | and represent the site of insertion of the hydrogenase.

FIG. 3 is the sequence of the PsaC-MeHydA fusion polypeptide (474 residues) (SEQ ID NO: 1). Highlighted residues indicate the PsaC fragment (green), N-terminus junction (cyan), HydA2 N-terminus linker sequence (magenta), and C-terminus linker (red).

FIG. 4 is the Clustal Omega (1.2.4) multiple sequence alignment of MeHydA to the mature (transit peptide removed) *Chlamydomonas reinhardtii* HydA1 and HydA2 hydrogenase sequences. (*) indicates fully conserved residues, (:) indicates residues with strongly similar properties, (.) indicates residues with weakly similar properties. Blue highlight shows the last conserved residue among all 3 sequences. MeHydA is SEQ ID NO: 13; HydA1 is SEQ ID NO: 14; HydA2 is SEQ ID NO: 15.

FIG. 7 is the Clustal Omega (1.2.4) multiple sequence alignment of PsaC-MeHydA with previously constructed chimeras. N-terminal junction is highlighted in blue, C-terminal junction is highlighted in red. PsaCMeHydA is SEQ ID NO: 1; PsaCMeHydA_null is SEQ ID NO: 16; PsaC-MeHydA2 is SEQ ID NO: 17; PsaCMeHydA1 is SEQ ID NO: 18;

Figure 1:
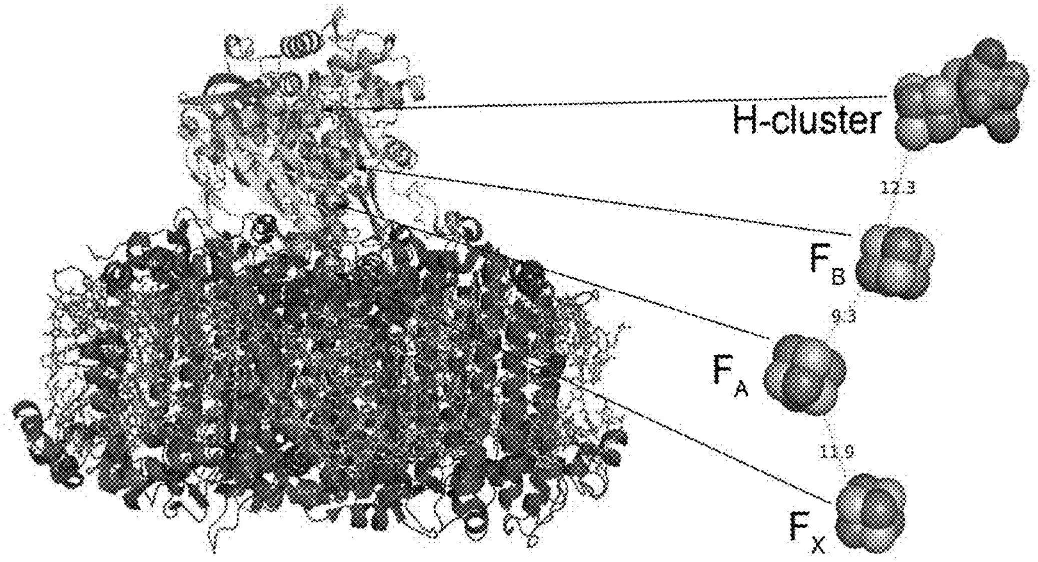
FIG. 1 presents a model of PSI-MeHydA. PsaA. Core subunits PsaA (red), PsaB (blue), PsaC-MeHydA (cyan), PsaD (yellow), PsaF (orange) are shown as cartoon representation, with pigments as green sticks and metallic clusters as space-filling models. On the right, an exploded view of the acceptor side cofactors (with edge-to-edge distances in Å) is shown.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The compositions and methods described herein are based, at least in part, on the inventor's development of a fusion of a photosystem I (PSI) protein and a heterologous iron-iron hydrogenase, created by insertion of a nucleotide sequence encoding a bacterial hydrogenase (e.g. HydA) sequence into or adjacent to a nucleotide sequence encoding a PSI protein (e.g. PsaC), and in vivo co-assembly of the PSI and hydrogenase portions. When expressed in algal cells, this PSI-HydA fusion protein increases molecular hydrogen ($H_2$) production under certain light conditions relative to unmodified algal cells. This means for $H_2$ production offers an ecologically-friendly, inexpensive renewable energy source.

The use of algal hydrogenases to produce $H_2$ in previously described PSI-HydA fusion proteins is limited by their oxygen sensitivity. Also, the $H_2$ production of PSI-HydA fusion proteins made with algal hydrogenases is also limited due to observed electron escape to ferredoxin/flavodoxin, which is thought to be due to escape from the hydrogenase domain. Given that algal hydrogenases must be able to bind and oxidize/reduce the algal ferredoxin, it was hypothesized that replacement with a bacterial hydrogenase that has not evolved to interact with chloroplast ferredoxin might result in less electron escape.

In a first aspect, this disclosure provides a genetically engineered cell comprising a polynucleotide encoding a fusion protein, the fusion protein comprising a photosystem I (PSI) protein, or a portion thereof, and a bacterial hydrogenase, or a portion thereof.

The engineered cell may be an algal cell or any cell capable of photosynthesis having PSI and a bacterial iron-iron hydrogenase. As used herein, the terms "genetically engineered" and "genetically modified" are used interchangeably and refer to a cell that includes an exogenous polynucleotide. In some cases, the cell has been engineered to comprise a non-naturally occurring nucleic acid molecule that has been created or modified by the hand of man (e.g., using recombinant DNA technology) or is derived from such a molecule (e.g., by transcription, translation, etc.). A cell that contains an exogenous, recombinant, synthetic, and/or otherwise modified polynucleotide is considered to be an engineered cell.

An engineered cell may be produced by introducing a recombinant nucleic acid molecule that encodes a PSI-HydA fusion protein of this disclosure. As used herein, the term "recombinant nucleic acid" or "recombinant polynucleotide" refers to a polynucleotide that is manipulated by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide. A recombinant nucleic acid molecule also can be based on, but manipulated so as to be different, from a naturally occurring polynucleotide, for example, a polynucleotide having one or more nucleotide changes such that a first codon, which normally is found in the polynucleotide, is biased for chloroplast codon usage, or such that a sequence of interest is introduced into the polynucleotide, for example, a restriction endonuclease recognition site or a splice site, a promoter, a DNA origin of replication, or the like.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). The polynucleotides may be cDNA or genomic DNA.

Polynucleotides homologous to the polynucleotides described herein are also provided. Those of skill in the art understand the degeneracy of the genetic code and that a variety of polynucleotides can encode the same polypeptide. In some embodiments, the polynucleotides (i.e., polynucleotides encoding the fusion polypeptides) may be codon-optimized for expression in a particular cell including, without limitation, a plant cell, bacterial cell, or algal cell. While particular polynucleotide sequences which are found in particular algae are disclosed herein any polynucleotide sequences may be used which encode a desired form of the polypeptides described herein. These represent non-naturally occurring sequences. Computer programs for generating degenerate coding sequences are available and can be used for this purpose. Pencil, paper, the genetic code, and a human hand can also be used to generate degenerate coding sequences.

The bacterial hydrogenase may be from *Megasphaera elsdenii* (MeHydA) or *Clostridium beijerinckii* hydrogenase (Cb5Ah). Compared to algal hydrogenases, the hydrogenase of *Megasphaera elsdenii* has been shown to be relatively $O_2$ tolerant, exhibiting a ~10-fold lower $O_2$ inactivation rate. The PSI protein may comprise one or more subunits of PSI (e.g., PsaA, PsaB, PsaC, PsaD, PsaE). In exemplary embodiments, the PSI protein is PsaC. The bacterial hydrogenase may be hydrogenase A (HydA). Any of the PSI subunits may be fused to HydA. Other bacterial Fe—Fe hydrogenases, and other oxygen-tolerant hydrogenases may be used. Other PsaC proteins may also be used. For example, 4 PsaC proteins from various algal species are provided in FIG. 2, and bacterial hydrogenase, MeHydA, is provided in FIG. 4. Any of these can be used in any combination to make the fusion proteins described herein.

Figure 5A:
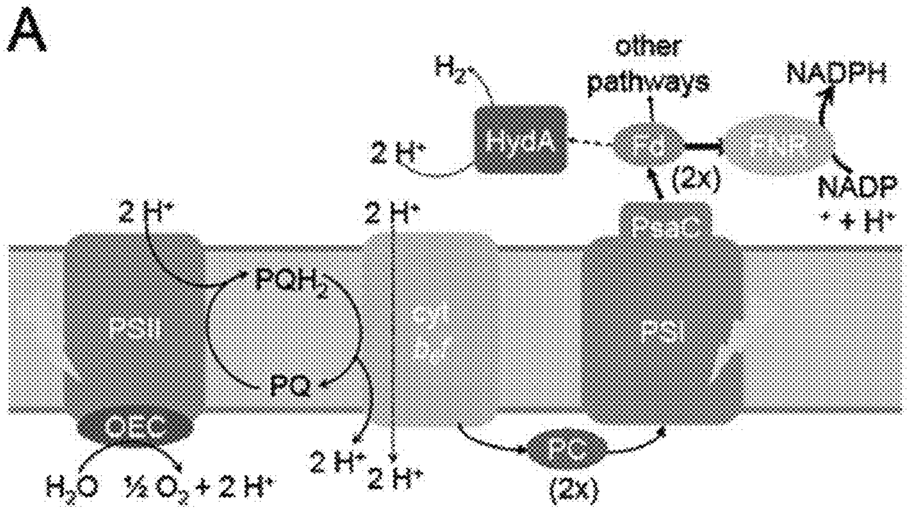
FIGS. 5A-5B present the photosynthetic electron transport chain (PETC) in WT cells (A) and the proposed system (B). (A) The PETC in the thylakoid membrane drives linear electron flow, with water being oxidized by the oxygen evolving complex (OEC) of PSII and Fd being reduced by PSI, accompanied by formation of proton motive force. Two electrons will exit the PETC for each $H_2O$ oxidized. Under most conditions, NADPH is the major product, made by FNR. $H_2$ is a minor and/or transient product under anoxic conditions. (B) In the system described here, bacterial hydrogenase (HydA) is directly attached to PSI, which should direct most electrons to $H_2$ production at the expense of Fd reduction.

A fusion protein comprising a bacterial hydrogenase or a functional portion thereof inserted into a PSI protein is also provided herein. "Fusion proteins" or "chimeric proteins" are proteins created through the joining of two or more genes that originally coded for separate proteins. Translation of this fusion gene results in a single or multiple polypeptides with functional properties derived from each of the original proteins. The fusion protein provided herein may be generated by inserting the nucleotide sequence encoding the hydrogenase (or a portion thereof) into or adjacent to the nucleotide sequence of one or more of the PSI subunits, thereby producing a recombinant nucleic acid molecule encoding a PSI-hydrogenase fusion protein. The nucleotide sequence encoding the hydrogenase may be inserted into or adjacent to a sequence encoding the PsaC subunit. The hydrogenase may be inserted in frame into the hinge region (shown as the β-hairpin in FIG. 2) of the PsaC subunit, such that the hydrogenase is positioned directly above the PsaC protein and captures the electrons produced by PSI. See FIG. 5. The hydrogenase is inserted into the PsaC in frame, such that the protein encoded by the polynucleotide contains the N-terminal portion of PsaC followed by the hydrogenase insertion and finally the C-terminal end of PsaC. The insertion of the hydrogenase into the PsaC protein can remove one or more amino acids from the hinge region of the PsaC protein. In the Examples, the insertion of the hydrogenase resulted in deletion of at least a few amino acids and/or insertion of a few linking amino acids as described more fully below. The deletion, addition or substitution of one, two, three, four, five, six, seven or up to 10 amino acids is contemplated. The additional amino acids may be flexible such as alanine, glycine or serine to allow for proper folding of the multi domain resulting fusion protein.

A "deletion" in a fusion polypeptide refers to a change in the amino acid sequence resulting in the absence of one or more amino acid residues. A deletion may remove at least 1, 2, 3, 4, 5, 10, 20, or more amino acids residues. A deletion may include an internal deletion and/or a terminal deletion (e.g., an N-terminal truncation, a C-terminal truncation or both of a reference polypeptide).

"Insertions" and "additions" in a fusion polypeptide refers to changes in an amino acid sequence resulting in the addition of one or more amino acid residues. An insertion or addition may refer to 1, 2, 3, 4, 5, 10, 20, 30, 40, or more amino acid residues. A variant of a polypeptide may have N-terminal insertions, C-terminal insertions, internal insertions, or any combination of N-terminal insertions, C-terminal insertions, and internal insertions.

One of skill in the art will appreciate that hydrogenases may be inserted into various PSI subunit proteins, e.g. PsaC hinge regions, and that the linking regions between the two protein portions could have altered amino acids, or the linkers could be of differing lengths.

In an exemplary embodiment, the fusion protein comprises the PsaC protein and the *Megasphaera elsdenii* hydrogenase (PsaC-MeHydA). The sequence of the PsaC-MeHydA fusion protein (SEQ ID NO: 1)
MAHIVKIYDTCIGCTQCVRACPLDVLEMVPWGG*ATATDAVP*NDVDKVKAA
LKDPEKIVIFQTAPAVRVGLGEAFGMDPGTFVEGKMVAALRTLGADYVED
TDFGADLTIMEEATELLHRLQSEEIPIPQFTSCCPAWVEFAETFYPDLLQ
HLSSTKSPISILSPVIKTYFAQQKNIDPKKIVNVCVTPCTAKKAEIRRPE
LSASGLFWDEPEIRDTDICITTRELAQWIQDENIDFASLEDSKFDKAFGE
ASGGGRIFGNSGGVMEAAIRTAYHMFTGRPAPKDFIPFEPVRGLQGVKKA
TVIFGHFVLHVAAISGLGNARAFIDDLIKNDAFEDYSFIEVMACPGGCIG
GGGQPKVKLPQVKKVQEARTASIYKSDEETDIKASWQNPEIETLYEAFLD
EPLSEMAEFTLHTHYSAGSGGGGSGAGGASQMASAPRTEDCVGCKRCETA
CPTDFLSVRVYLGSESTRSMGLSY.

The singly underlined residues indicate the PsaC fragments; the doubly underlined residues are the N-terminal junction; the italicized residues are a HydA2 N-terminus linker; and the bold residues are a C-terminal linker.

In another exemplary embodiment, the fusion protein comprises the PsaC protein and the *Clostridium beijerincki* hydrogenase PsaC-CbA5H. The sequence of the *Clostridium beijerincki* hydrogenase CbA5H protein is:

(SEQ ID NO: 11)
MGDNKKSFIQSALGSVFSVFSEEELKELSNGRKIAICGKVNNPGIIEVPE
GATLNEIIQLCGGLINKSNFKAAQIGLPFGGFLTEDSLDKEFDFGIFYEN
IARTIIVLSQEDCIIQFEKFYIEYLLAKIKDGSYKNYEVVKEDITEMFNI
LNRISKGVSNMREIYLLRNLAVTVKSKMNQKHNIMEEIIDKFYEEIEEHI
EEKKCYTSQCNHLVKLTITKKCIGCGACKRACPVDCINGELKKKHEIDYN
RCTHCGACVSACPVDAISAGDNTMLFLRDLATPNKVVITQMAPAVRVAIG
EAFGFEPGENVEKKIAAGLRKLGVDYVFDTSWGADLTIMEEAAELQERLE
RHLAGDESVKLPILTSCCPSWIKFIEQNYGDMLDVPSSAKSPMEMFAIVA
KEIWAKEKGLSRDEVTSVAIMPCIAKKYEASRAEFSVDMNYDVDYVITTR
ELIKIFENSGINLKEIEDEEIDTVMGEYTGAGIIFGRTGGVIEAATRTAL
EKMTGERFDNIEFEGLRGWDGFRVCELEAGDIKLRIGVAHGLREAAKMLD
KIRSGEEFFHAIEIMACVGGCIGGGGQPKTKGNKQAALQKRAEGLNNIDR
SKTLRRSNENPEVLAIYEKYLDHPLSNKAHELLHTVYFPRVKKD.

The amino acid sequence of the PsaC-CbA5H fusion protein is:

(SEQ ID NO: 12)
MAHIVKIYDTCIGCTQCVRACPLDVLEMVPWGG*ATATDAVP*NTMLFLRDL
ATPNKVVITQMAPAVRVAIGEAFGFEPGENVEKKIAAGLRKLGVDYVFDT
SWGADLTIMEEAAELQERLERHLAGDESVKLPILTSCCPSWIKFIEQNYG
DMLDVPSSAKSPMEMFAIVAKEIWAKEKGLSRDEVTSVAIMPCIAKKYEA
SRAEFSVDMNYDVDYVITTRELIKIFENSGINLKEIEDEEIDTVMGEYTG

-continued

```
AGIIFGRTGGVIEAATRTALEKMTGERFDNIEFEGLRGWDGFRVCELEAG
DIKLRIGVAHGLREAAKMLDKIRSGEEFFHAIEIMACVGGCIGGGGQPKT
KGNKQAALQKRAEGLNNIDRSKTLRRSNENPEVLAIYEKYLDHPLSNKAH
ELLHTVYFPRVKKDSGAGGASQMASAPRTEDCVGCKRCETACPTDFLSVR
VYLGSESTRSMGLSY.
```

The singly underlined residues indicate the PsaC fragments; the doubly underlined residues are the N-terminal junction; the italicized residues are a N-terminus linker.

The fusion protein/polypeptide may comprise SEQ ID NO: 1 or 12, or a sequence having at least 90, 92, 94, 95, 96, 97, 98, 99 percent identity to the fusion protein/polypeptide of SEQ ID NO: 1 or 12. In particular the amino acids in bold, italics or double underlined in SEQ ID NO: 1 or 12 may be altered to provide additional linking regions between the portions of the fusion protein.

Protein and nucleic acid sequence identities may be evaluated using the Basic Local Alignment Search Tool ("BLAST") which is well known in the art (Karlin and Altschul, 1990, Proc. Natl. Acad. Sci. USA 87: 2267-2268; Altschul et al., 1997, Nucl. Acids Res. 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user. Methods of amino acid sequence alignment are well-known. Some alignment methods take into account conservative amino acid substitutions. Such conservative substitutions, generally preserve the charge and hydrophobicity at the site of substitution, thus preserving the structure (and therefore function) of the polypeptide.

The phrases "% sequence identity," "percent identity," or "% identity" refer to the percentage of residue matches between at least two amino acid sequences aligned using a standardized algorithm. For example, reference to "at least 95% sequence identity to SEQ ID NO: 1 or SEQ ID NO: 12," refers to alternative embodiments with at least 95% identity, at least 96% identity, at least 97% identity, at least 98% identity, or at least 99% identity to the amino acid sequence of SEQ ID NO: 1 or SEQ ID NO: 12. Percent identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, may be used to describe a length over which percentage identity may be measured.

Any appropriate technique for introducing recombinant nucleic acid molecules into algal cells may be used. Techniques for nuclear and chloroplast transformation are known and include, without limitation, electroporation, biolistic transformation (also referred to as micro-projectile/particle bombardment), agitation in the presence of glass beads, and *Agrobacterium*-based transformation. Accordingly, a recombinant nucleic acid molecule encoding a PsaC-MeHydA fusion protein may be introduced into an algal cell by, for example, electroporation, by particle bombardment, by agitation in the presence of glass beads, or by *Agrobacterium*-based transformation. With chloroplast transformation, transgenes can be easily directed to integrate via homologous recombination. Nuclear transformation usually results in random integration events. In some embodiments the native psaC and hydA genes are mutated and/or replaced with the fusion protein in the cells such that all copies of PSI in the cell contain the fusion protein.

By way of example, described herein is introduction of a nucleic acid encoding a psaC-hydA fusion protein into an algal cell's chloroplast genome by particle-mediated gene transfer. In this example, flanking sequences were used to direct homologous recombination such that the recombinant nucleic acid replaces the endogenous psaC gene.

Any appropriate method can be performed to confirm introduction and expression of recombinant nucleic acids in the modified cell. For instance, polymerase chain reaction (PCR) or PCR-based methods can be used to verify replacement of psaC by psaC-MeHydA. Amplified products may be sequenced to ensure that no mutations are found in the recombinant nucleic acid as a result of the cloning process.

After the PSI-HydA fusion protein is expressed in the cell, hydrogenase activity may be measured. Any appropriate means of measuring hydrogenase activity may be used. Samples may be collected for analysis of hydrogenase activity by gas chromatography (GC). Those of skill in the art are aware of methods to measure hydrogenase activity and such methods are provided in the Examples.

The PSI-HydA fusion protein may be expressed in any cell comprising a chloroplast or using photosystem I for photosynthesis. For example, plant cells, algal cells, or cyanobacteria may be used. The cell must also have or be engineered to have the maturase proteins, HydE/F/G. The Fe—Fe hydrogenases for use in the methods suitably have a structure similar to MeHydA, in which the N-terminal and C-terminal ends of the protein are in proximity to each other or the hydrogenases are modified via truncation such that the N-terminal and C-terminal ends of the protein are in proximity to each other. Those of skill in the art can use protein modeling programs or crystal structures of hydrogenases to determine appropriate hydrogenases for use in the methods, cells and constructs provided herein.

The terms "algal cell" or "algae" as used herein refer to unicellular, photosynthetic, oxygenic algae. They are non-parasitic plants without roots, stems or leaves; they contain chlorophyll and have a great variety in size, from microscopic to large seaweeds. Green algae, belonging to Eukaryota-Viridiplantae-Chlorophyta-Chlorophyceae, can be used. Blue-green, red, or brown algae may also be used.

Exemplary algae for which the compositions and methods described herein includes those of the genus *Chlamydomonas*. In some embodiments, the engineered algal cells are unicellular green alga of the species *Chlamydomonas reinhardtii*, for which the sequence of all three genomes (nuclear, chloroplast and mitochondria) has been determined. Algal cells of the genus *Chlorella* and other genera may be used in other embodiments. For example, the PsaC of *Chlorella vulgaris, Picochlorum soloecismus*, or *Cyanidioschyzon merolae* may be used. These PsaC proteins are described in U.S. Publication No. US20220204996A1, which is incorporated by reference in its entirety. Algal cells of *Galdieria sulphuraria* may also be used. Iron-Iron hydrogenases from any of these algal species may be inserted into the hinge region of the PsaC in the same or similar manner as shown in the Examples for *Chlamydomonas.*

In the Examples, the polynucleotide encoding the fusion protein was integrated into the native PsaC gene within the chloroplast genome via homologous recombination. A similar fusion protein can be recombined into the chloroplast genome of any cell containing a chloroplast, such as algal cell or plant cells. A similar fusion protein and polynucleotide encoding the same may be used in the cyanobacteria to engineer cyanobacteria cells capable of generating increased hydrogen.

In a second aspect, provided herein is algal biomass comprising genetically engineered algal cells of the disclosure. In particular, provided herein is algal biomass that contains genetically engineered algal cells that exhibit increased hydrogen production on particular growth (e.g., light) conditions relative to genetically unmodified algal cells or other controls when cultured under the same conditions. As used herein, the term "algal biomass" refers to the amount or density of algae in a given area or volume (e.g., of water or other liquid) at a given time. Algal biomass encompasses algae grown in various cultivation systems such as photoreactors and open ponds, but also algal material obtained from different types of waste from industry and sewage plants.

In a third aspect, provided herein is an expression cassette that drives expression of a fusion protein comprising a PSI protein and a bacterial hydrogenase. The expression cassette may comprise a promoter operably linked to a nucleic acid sequence that encodes a fusion protein comprising a PSI protein and a bacterial hydrogenase. In preferred embodiments, the nucleic acid is a recombinant nucleic acid that encodes a PSI-MeHydA fusion protein, such as the fusion protein of SEQ ID NO: 1. While PSI is encoded in the chloroplast, the gene and thus the fusion protein may be encoded in the nucleus, added as an additional copy in the chloroplast or even encoded on an extra chromosomal expression cassette such as a plasmid or artificial chromosome. In these alternative expression cassettes, the promoters may be selected based on the expression system being contemplated by those of skill in the art. For example, as demonstrated in Reifschneider-Wegner et al.[44] the hydrogenase can be expressed in chloroplasts using the psbD promoter/5'UTR to drive expression of the chloroplast-optimized hydA gene. A similar system could be used for expression of the fusion protein described herein.

Constructs are also provided herein. As used herein, the term "construct" refers to recombinant polynucleotides including, without limitation, DNA and RNA, which may be single-stranded or double-stranded and may represent the sense or the antisense strand. The constructs provided herein may be prepared by methods available to those of skill in the art. The constructs and expression cassettes provided herein are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs and expression cassettes provided herein may include a promoter operably linked to any one of the polynucleotides described herein but need not have a promoter and may be used for homologous recombination into the native site of psaC in the algae. Alternatively, the constructs may include a promoter and the promoter may be a heterologous promoter or an endogenous promoter associated with the PsaC polypeptide.

As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed polynucleotides are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may affect transcription of the polynucleotides. The polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter.

In a fourth aspect, provided herein are methods for increasing hydrogen ($H_2$) production in a cell. The method comprises introducing into the cell a polynucleotide or an expression cassette comprising the polynucleotide encoding a fusion protein comprising a PSI protein and a bacterial hydrogenase described herein, and culturing the cell under continuous illumination (e.g. saturating light conditions). The cell may be cultured in a bioreactor growth system and the gas released during growth can be collected, removed from the bioreactor, and the hydrogen can be separated and collected from the remaining air in the bioreactor. The cell may be an algal cell.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

As used herein, the terms "optional" or "optionally" mean that the subsequently described event or circumstance may or may not occur, and that the description includes instances where said event or circumstance occurs and instances where it does not.

The present invention has been described in terms of one or more preferred embodiments, and it should be appreciated that many equivalents, alternatives, variations, and modifications, aside from those expressly stated, are possible and within the scope of the invention.

EXAMPLES

Example 1—In Vivo Fusion of Photosystem I (PSI) and Bacterial Hydrogenase

Figure 5B:
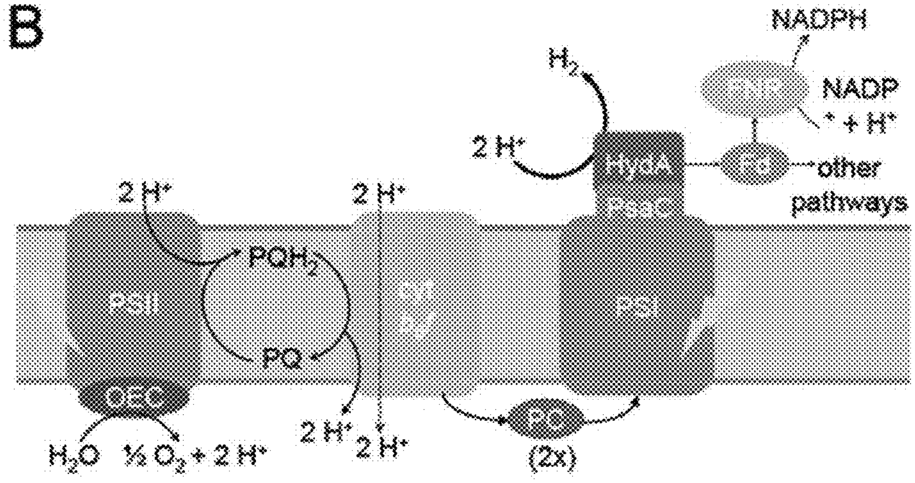

Using a unicellular green alga (*Chlamydomonas reinhardtii*) as an experimental system, an in vivo fusion of PSI and the [FeFe] hydrogenase expressed by *Megasphaera elsdenii* was created (see FIGS. 1 and 5B). While the structural gene for this hydrogenase is in the nuclear genome and the core photosystem subunits are chloroplast encoded, it has been shown that active hydrogenase can be made from a gene transplanted into the chloroplast chromosome. The data presented in this section demonstrate that photosynthetic flow in the re-engineered chloroplast results in biohydrogen production (see FIG. 5B).

Experimental Design

Chimeric protein design and modeling: A protein sequence of PsaC-MeHydA is shown in FIG. 3. MeHydA sequence[25] (GenBank accession number AAF22114.1) was aligned with the *Chlamydomonas reinhardtii* HydA1 GenBank accession number AAG00591.1) and HydA2 (GenBank accession number AAR04931.1) protein sequences (lacking transit peptide) (see FIG. 4) with the use of Clustal Omega tool[26] (https://www.ebi.ac.uk/Tools/msa/clustalo/). The MeHydA domain is very different from the algal hydrogenases: 30.7% identity (43.1% similarity) against HydA1 and 31.5% identity (43.0% similarity) against HydA2. It has previously been shown that CpIHydA from *Clostridium pasteurianum* could be expressed and activated in the algal chloroplast in vivo[39], so it was not unrealistic to expect that another bacterial HydA domain could also be activated by the algal HydEF/HydG maturases. However, since MeHydA shares only 31.3% sequence identity (41.4% similarity) with CpIHydA, it was not guaranteed that the algal maturation machinery could insert the H-cluster into this foreign hydrogenase.

A model of the MeHydA was generated with Phyre$^2$ server[27]. The first 80 residues of MeHydA correspond to the ferredoxin domain and residues past the last conserved residue among all 3 hydrogenases (highlighted in FIG. 4) were removed in PyMOL[28]. In preparation for docking, PsaC residues D32-K35 of the *Chlamydomonas reinhardtii* PSI structure (PDB ID: 6JO5[29]) were also removed in PyMOL. A rigid body docking of the truncated *Megasphaera elsdenii* hydrogenase domain (set as ligand) to the PsaA, PsaB, PsaF and the modified PsaC subunits (set as receptor) was performed in the ClusPro2 server[30] using a single distant restraint 1-25 Å between C14 of PsaC and C383 of MeHydA (original numbering). The most plausible docked model was used in design of the linking sequences. For N-terminus MeHydA junction with PsaC, a 10 amino acid residue (GGATATDAVP (SEQ ID NO: 13)) linking sequence was used similarly to PsaC-HydA2 and PsaC-HydA1 constructs. For C-terminus junction of MeHydA, a 15 amino acid long sequence (HYSAGSGGGGSGAGG) (SEQ ID NO: 2). A final model was built using Robetta's web server comparative modeling algorithm[31] providing the docked model coordinates as a template.

Figure 6:
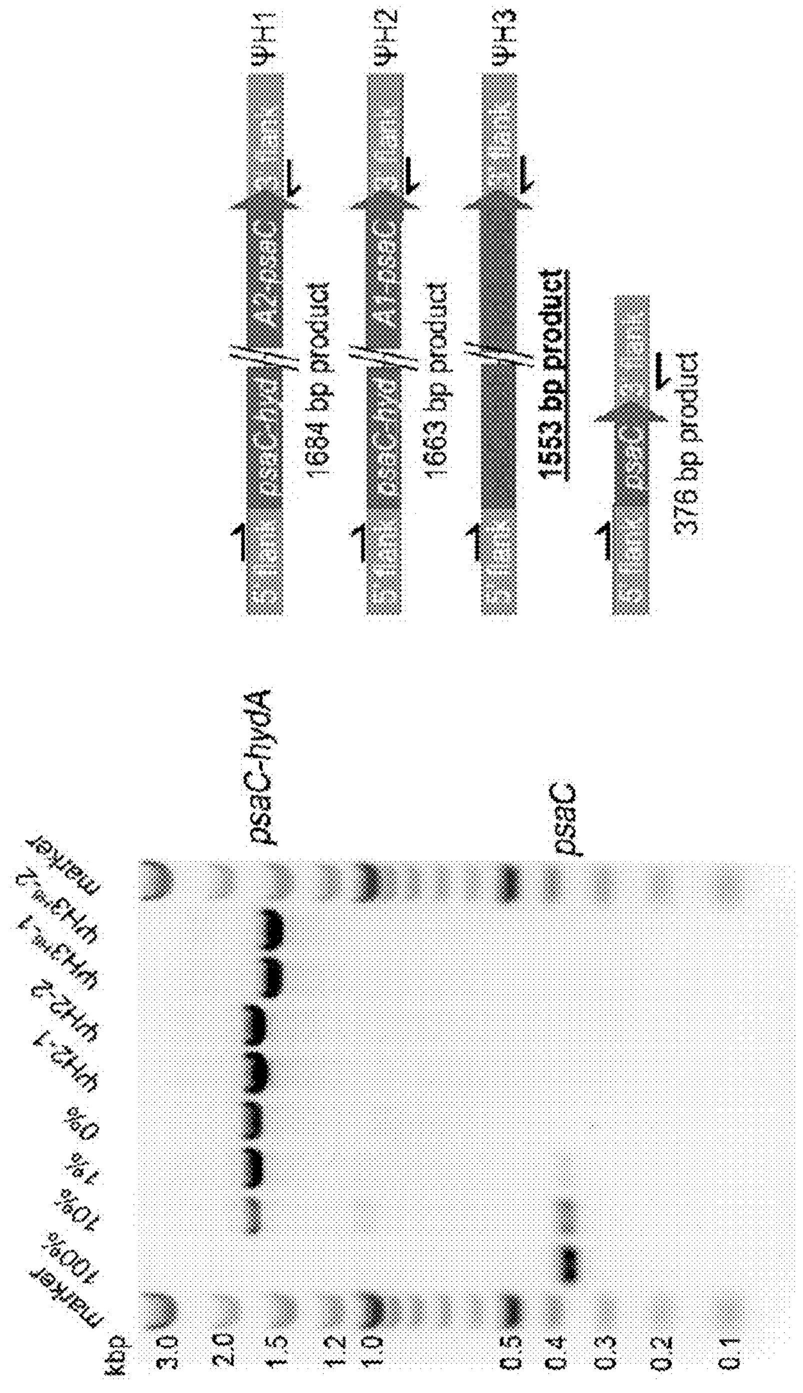
FIG. 6 is an agarose gel image of homoplasmicity detection PCR. Wild type genomic DNA (WTH6) indicated as a percentage of total DNA (diluted into ΨH1 genomic DNA containing psaC-HydA2 in place of psaC). ΨH2 genomic DNA is shown for comparison. Total DNA per reaction was 100 ng.

Generation of PSI-MeHydA algal mutants: The psaC-MeHydA fusion gene sequence was codon optimized for chloroplast expression and synthesized by Genscript (Piscataway, NJ USA). The gene construct was delivered on pBS-EP 5.8 vector[32], in which the fusion gene replaced the psaC gene. Transformations were carried out in the PBC4-$2^{H6}$ strain lacking psaC and having hexahistidine tag on exon 1 of psaA[33] via biolistic transformation as previously described[17]. Positive transformants were selected on Tris-acetate-phosphate (TAP) plates with 100 mg $L^{-1}$-spectinomycin in the dark. Positive transformants were confirmed by PCR with region specific primers (PsaC5': TAATATGGAGATGACATATTTAG (SEQ ID NO: 3) and PsaC3': GATCTCAC CAAGATACTCCC (SEQ ID NO: 4). See FIG. 6.

Growth conditions: All algae strains were grown on liquid Trisacetate-phosphate (TAP) medium with revised mineral nutrient supplement[34]. Mutants on plates were kept in the dark. Liquid cultures were grown under low room light (5-10 μmol $m^{-2}$ $s^{-1}$ PAR).

Chlorophyll (Chl) measurement: Concentrations of Chl a and b were determined in 80% acetone as previously described[35].

Thylakoid and PSI preparation: Thylakoid membranes and PSI preparations were done as previously described[17] with minor modifications outlined below.

In the cell lysis step, ultrasonic cell disruption or French pressure cell was used. For ultrasonic cell disruption, cell pellet (from 10 L mid-late log phase cultures, equivalent of 80-100 mg of Chl) was resuspended in breaking buffer (50 mM HEPES-KOH pH 7.5, 0.3 M sucrose, 10 mM EDTA-KOH, 1 mM phenylmethyl sulfonyl fluoride (PMSF)) to a final volume of 200 mL. Ultrasonic lysis was done in a thin-walled aluminum cup on ice with continuous stirring in the dark. Temperature was continuously monitored during sonication and was always at 4° C. Branson sonifier S-450 was operated with ½" (12.7 mm) catenoidal horn at amplitude level 3 (10% duty cycle) for 60 min. It approximately corresponded to 800 J per 10 mL of lysate as recommended for complete breakage of algal cells[36]. The lysate was spun down at 64000×g at 4° C. for 15 min, washed with H2 buffer (5 mM HEPES-KOH pH 7.5, 0.3 M sucrose, 10 mM EDTA-KOH) and resuspended in buffer H3 (5 mM HEPES-KOH, 1.8 M sucrose, 10 mM EDTA-KOH). All the following steps of discontinuous sucrose gradient were as previously described[17].

French press lysis protocol was followed exactly as previously described[17].

PSI isolation was done oxically using PROTEINDEX™ Ni-Penta™ agarose resin (Marvelgent Biosciences) as previously described[33]. For oxygen removal, PSI elution samples were concentrated and exchanged buffer using Amicon™ stirred ultrafiltration cell (furnished with 100 kDa MWCO regenerated cellulose disc) inside the glovebox with a degassed solubilization buffer (25 mM HEPES-KOH, pH 7.5, 300 mM KCl, 5 mM $MgSO_4$, 10% glycerol, 0.03% n-dodecyl-β-D-maltoside (β-DDM)).

Laser-flash spectroscopy: Thylakoids were resuspended at ~60 μg Chl $ml^{-1}$ in 25 mM HEPES-KOH (pH 7.5), 300 mM KCl, 10% glycerol, 5 mM sodium ascorbate while PSI were resuspended at ~6 μg Chl $ml^{-1}$ in with the same buffer with 0.03% β-DDM. Samples were kept on ice in the dark before measurements. Absorbance changes pumped by a saturating laser flash (532 nm, 6 ns, 20-25 mJ) were monitored at 696 nm with weak LED pulses (10 μs) using JTS-10 (Bio-Logic) kinetic spectrophotometer. Background transients were collected by running the same sequence with laser shutter closed.

Gas chromatography (GC) measurements: A model SRI 310 gas chromatograph with thermal conductivity detector and 5 Å molecular sieve prepacked column (91.4 cm long) was used. Gas tight syringes (1700 series) with non-coring needles were used for probing headspace.

Immunoblotting: Western blots were carried out as previously described[17]. Solubilized thylakoids were loaded on the same Chl (2 μg).

Membrane inlet mass spectrometry (MIMS) measurements: MIMS measurements were carried out as previously described[18].

Flavodoxin photoreduction assay: The experiment was carried out as described in Kanygin et al.[18], with one major difference—no oxygen was expected as it was set up in the anaerobic chamber filled with 5% H2/95% N2 (Coy).

In vivo $P_{700}$ photobleaching and fluorescence measurements: Early log phase cells were washed and then resuspended in 10 mM sodium phosphate (pH 7.0), 2 mM sodium bicarbonate and 20% Ficoll™ PM400 (GE Healthcare) to ~30 μg/mL Chl ($P_{700}^+$) or ~9 μg Chl $mL^{-1}$ (for Chl fluorescence measurements). Cells were dark adapted for 5 min. Aerobic conditions were ensured by occasional mixing and brief sparging with air (in between the measurements). $P_{700}^+$ signal was measured at 696 nm as previously described[17]. Chlorophyll steady state fluorescence was measured after 2 min of green LED (520 nm) of variable intensity as previously described 18.

Results and Discussion

Design and expression of PSI-MeHydA: To generate a reasonable model of PSI-MeHydA, the hydrogenase domain of the MeHydA homology model was isolated based on the work of Caserta et al.[37] and a multiple sequence alignment with CrHydAs (FIG. 4). The first 80 residues corresponding to a ferredoxin-like domain were removed, as well as all residues past the last consensus residue (T452, FIG. 4). The model of the truncated MeHydA hydrogenase domain was docked to a modified PsaC, PsaA, PsaB and PsaF subunits of PSI (PDB ID:6JO5[29]) with a single distant restraint (1-25 Å) between proximal to the surface cysteines of $F_b$ and H-cluster. The most plausible model (obtained with balanced coefficients) was found to have N-terminal junction residues of 2 domains to be ~12 Å apart from each other, while the C-terminal junction was ~22 Å apart. For the N-terminal junction, the native N-terminus sequence connecting hydrogenase and F-domains with added G (GGAIVE) (SEQ ID NO: 5) was tried, while a YFSDKSGG (SEQ ID NO: 6) sequence was used for the C-terminus junction. When introduced into *Chlamydomonas reinhardtii*, no stable chimeric PSI-MeHydA complex was detected (see FIG. 7 for multiple sequence alignment of various PsaCHydA). The mutant was unable to accumulate any PSI-HydA chimera: there was no PSI, no hydrogenase activity, and no photobiological hydrogen production. For the second attempt, the N-terminal linker was made slightly longer. The same linker was used in the previously made chimeras (See FIG. 3, magenta region). The C-terminal junction was also made more like the previously made chimeras by replacing YF with HY and extending the length of the linker by 7 amino acid residues compared with the N-terminal linker. A model of this version of PSI-MeHydA is shown in FIG. 1. These modifications resulted in a stably assembled PSI-MeHydA, present at 25%-67% of the WT PSI level. The model shows that the terminal iron sulfur cluster of PSI ($F_B$) could be as close as 12.3 Å (edge-to-edge) to the iron-sulfur cubane of the H-cluster (FIG. 1). This is closer than in previously published models for PSI-HydA2 (14.8 Å) or PSI-HydA1 (15 Å). This difference could be due to the smaller MeHydA domain: the truncated polypeptide is 41 residues shorter than algal HydA1 trimmed of N- and C-terminal nonconserved residues. The structural similarity of PsaC to the F-domain of MeHydA might play a role in such a close docking, in that one ferredoxin-like domain is being replaced with another, albeit with a different connectivity. Based on Marcus electron transfer theory, the forward electron transfer rate in the PSI-MeHydA chimera might be faster than in the previously designed chimeras, assuming that the reorganization energy and driving force of the reaction are not significantly different.

The designed psaC-hydA gene was delivered to the chloroplast of the PBC4-2 strain, which lacks the psaC gene and harbors a $His_6$-tagged version of psaA, by particle bombardment. Transformants were selected for spectinomycin/streptomycin resistance. Homologous recombination with the chloroplast chromosome should result in replacement of psaC with the psaC-hydA gene. Positive transformants were confirmed by PCR with region-specific primers (FIG. 6) and Sanger sequencing of the amplicons. For brevity, PBC4-2 [PsaC-MeHydA] will be referred to as $\Psi H3^{H6}$, and PBC4-2[pBSEP5.8] expressing wild type psaC as $WT^{H6}$.

Figures 8A, 8B:
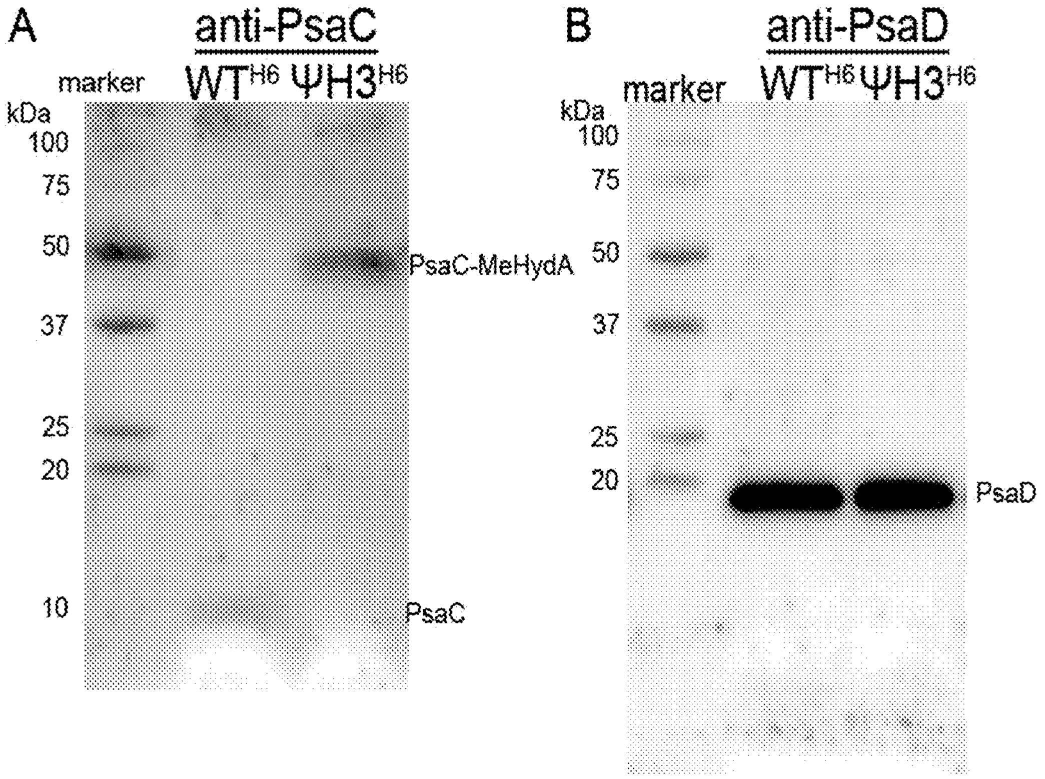
FIGS. 8A-8B present immunoblots of solubilized thylakoids, loaded on equal amount of Chl (2 μg) and probed with antibodies against PsaC (A) or PsaD (B).

Expression of PsaC-MeHydA was confirmed by Western blot using solubilized thylakoids prepared from aerobically grown cells (FIG. 8). Samples were loaded on equal Chl amounts (2 μg per lane). When the blot was probed with anti-PsaC antibodies (FIG. 8A), the $WT^{H6}$ lane showed a single 10 kDa band corresponding to the PsaC subunit. A single ~50 kDa band appeared in the $\Psi H3^{H6}$, which is most likely the band corresponding to PsaC-MeHydA (predicted MW=51.2 kDa). It was also confirmed that the PsaD subunit is present in thylakoids of $\Psi H3^{H6}$ (FIG. 8B). Given that PsaD is an extrinsic subunit of PSI, this indicates that PsaD is assembled onto the PSI-MeHydA complex, as seen before for PSI-HydA1 and PSI-HydA2.

Spectroscopic Characterization of the PSI-MeHydA

A primary function of reaction centers—conversion of absorbed light energy into a stable charge separation—requires all cofactors of the electron transfer chain to be assembled. The PsaC domain of PsaC-MeHydA carries two terminal [Fe4S4] clusters: $F_A$ and $F_B$. They can only be inserted upon proper folding of the PsaC domain from the first 30 and last 46 residues of the chimeric polypeptide. To test assembly and accumulation of PSI-MeHydA, thylakoids were prepared oxically via 2 methods: ultrasonic cell disruption and French Press. The former has the advantage of potentially being used under complete anoxia (inside the glovebox), while the latter is a standard thylakoid preparation.

Figures 9A, 9B:
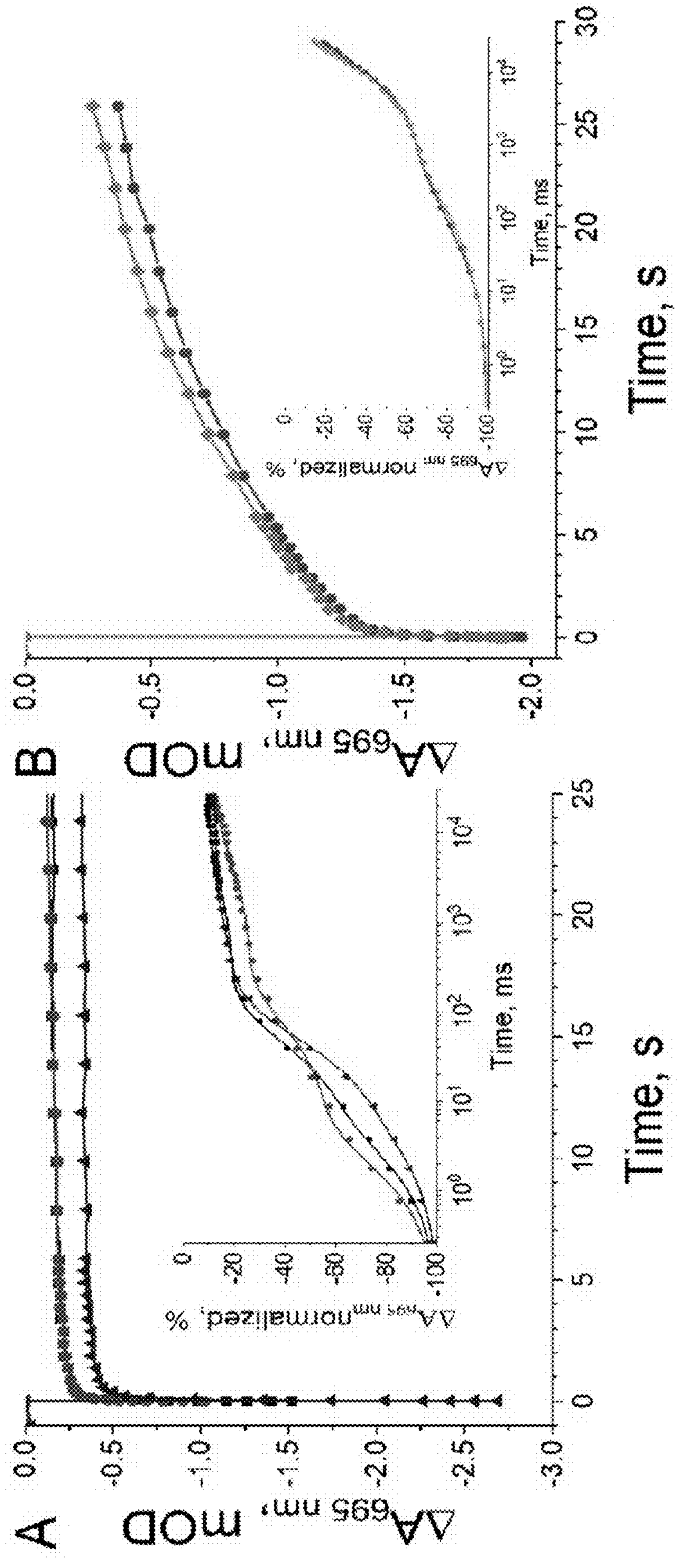
FIGS. 9A-9B present $P_{700}$ photooxidation and recovery in thylakoids ($WT^{H6}$—black squares, $ΨH3^{H6}$-1—red circles, $ΨH3^{H6}$-2—green diamonds, JVD-$1B^{H6}$—blue triangles), prepared anoxically via sonication protocol (A) or French press protocol in air (B). Transients normalized to 60 μg/ml of Chl. Insets show dark reduction of $P_{700}^+$ with time shown on a log-scale. Average of 3 technical replicates.

First, the amplitude of $P_{700}^+$ formation was observed in thylakoids prepared via sonication. After a saturating laser flash in the presence of ascorbate (to ensure P700 is reduced before the flash), accumulation of PSI-MeHydA relative to the $WT^{H6}$ signal was observed (FIG. 9A). Since $WT^{H6}$ mutant was made of the photosynthetically inactive PBC4-2 strain lacking psaC, which was maintained heterotrophically for some time, another WT control—JVD-$1B^{H6}$ was tested. When amplitudes of $P_{700}^+$ in thylakoids are compared between $\Psi H3^{H6}$ and JVD-$1B^{H6}$, ~38% relative photoaccumulation of the chimera is observed. Using an ultrasonic cell disruption protocol providing 800 J/10 mL of lysate[36], despite precautions aimed at reducing global temperature rise of the solution (and no such rise was detected in 200 mL of lysate solution at any point during cell lysis), the Chl/$P_{700}^+$ ratio for $\Psi H3^{H6}$, $WT^{H6}$ and JVD-$1b^{H6}$ were 6540, 4390 and 2480, respectively.

Figure 10:
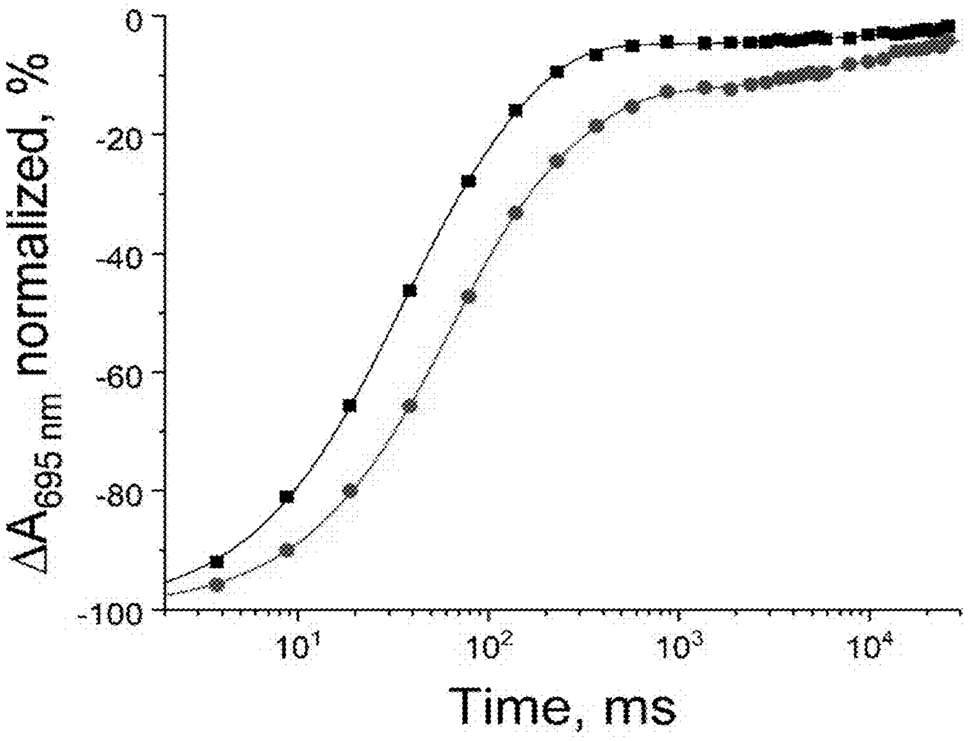
FIG. 10 presents recovery kinetics of $P_{700}^+$ in purified PSI from thylakoids in FIG. 9A ($WT^{H6}$—black squares, $ΨH3^{H6}$—red circles). Samples were set up anoxically. Transients represent average of 3 technical replicates.

In thylakoids prepared by French press (FIG. 9B), a ~2 times larger amplitude of $P_{700}^+$ and a lower Chl/$P_{700+}$ ratio (3410 and 3520) was observed for two independent transformants of $\Psi H3^{H6}$. When compared with previously made chimeras (prepared with French press protocol): 5650 for PSI-HydA2 (~15%), 1100 for PSI-HydA1, PSI-MeHydA accumulation is at 24-25% of typical WT level. The relatively high Chl/$P_{700+}$ is using the sonication protocol is likely due to local hot spots formed upon resonant bubble implosions, following sonolysis of water[40] (formation of OH· and H· radicals—strong oxidant and reductant) resulting in partial protein damage and faster charge recombination reactions in the affected reaction centers (if electron transfer chain is cut short). It is possible that faster charge recombination reactions were partially due to a strong reductant generated in the process of sonolysis of water since very fast phase of charge recombination in the purified PSI is not observed (see FIG. 10, Table 2). The ratio of Chl/$P_{700}^+$ of ~430 ($PSI^{H6}$) and ~690 ($PSI^{H6}$-MeHydA) suggests that purified PSI from sonicated cells have some inactive reaction centers as a mere contribution from PSI-LHCI (219 Chl/$P_{700}^+$, PDB ID: 6JO5) or even PSI-LHCI-LHCII (332 Chl/$P_{700}^+$, PDB ID: 7D0J) cannot explain such a high ratio. A typical PSI IMAC purification from French Pressed algal cells doesn't exceed 220 Chl/$P_{700}^+$ and usually less.

Second, the decay of $P_{700}^+$ signal in the dark was examined. Upon charge separation in the absence of available electron acceptors, the reduced iron sulfur clusters of PSI harbored by PsaC will eventually backreact with $P_{700}^+$. Charge recombination of the $P_{700}^+$ ($F_A$/$F_B$)-state typically happens with a time constant(s) of 40-200 ms and if $F_AF_B$ are not available (e.g., PsaC is absent or $F_A$/$F_B$ is reduced), charge recombination from $F_{X-}$ would happen with a time constant of ≤1 ms[38]. The $P_{700}^+$ transients (see FIGS. 3A and B insets) were fitted to a triexponential decay function. The parameters are shown in Table 1 below. All preparations exhibited a component corresponding to charge recombination of $P_{700}^+$ (FA/FB)-, confirming that the PsaC domain had folded correctly.

TABLE 1

Fitting coefficients of P700+ decay in thylakoids

| Parameter | Sonication protocol | | | French press protocol | |
|---|---|---|---|---|---|
| | $WT^{H6}$ | JVD-$1b^{H6}$ | $\Psi H3^{H6}$-1 | $\Psi H3^{H6}$-1 | $\Psi H3^{H6}$-2 |
| $\tau_1$ (ms) | 2.3 ± 0.3 | 2.3 ± 0.4 | 2.0 ± 0.3 | 23.4 ± 4.5 | 13.9 ± 3.1 |
| $A_1$ (%) | 30 ± 1.4 | 16.5 ± 1.2 | 41 ± 1.8 | 11.4 ± 1.5 | 8.0 ± 0.9 |
| $\tau_2$ (ms) | 47 ± 3 | 52 ± 2.5 | 76 ± 9 | 192 ± 21 | 184 ± 13 |
| $A_2$ (%) | 50 ± 1.3 | 61.5 ± 1.2 | 32 ± 1.4 | 19 ± 1.4 | 22.4 ± 1 |
| $\tau_3$ (s) | 2.9 ± 0.4 | 0.85 ± 0.2 | 5.5 ± 0.9 | 15.2 ± 0.6 | 16.4 ± 0.6 |
| $A_3$ (%) | 9.9 ± 0.6 | 9.6 ± 1 | 14 ± 0.8 | 60 ± 1 | 69 ± 1 |
| $A_0$ (%) | 10.1 ± 0.3 | 12.6 ± 0.2 | 12.8 ± 0.6 | 8.1 ± 1.1 | 0.3 ± 1.2 |
| $R^2$ | 0.99895 | 0.99941 | 0.9968 | 0.99964 | 0.9997 |

Of note, all thylakoids prepared via sonication show signs of shorter decay time constants than expected from a typical $P_{700}^+$-(FA/FB)- and likely result from some fraction of reaction centers having lost PsaC-MeHydA. The slowest decay component (on the order of seconds) is due to $P_{700}^+$ being reduced by ascorbate, because electrons had escaped from the iron sulfur clusters to exogenous acceptors (such as $O_2$). This phase was especially prevalent in the French press preparations (60-70% amplitude) while also present in the ultrasonically disrupted cells (10-15% amplitude).

To get rid of dissolved oxygen, PSI prepared from sonicated thylakoids under anoxia were concentrated. In $P_{700}$ bleaching and recovery kinetic experiment (FIG. 10), a diminished slow phase was observed (3-10% amplitude, see Table 2 below). $WT^{H6}$ PSI showed a typical biphasic kinetic (24 ms and 98 ms) for charge recombination $P_{700}^{+}$-(FA/FB)-. PSI-MeHydA sample on the other hand showed biphasic kinetics that are significantly slower than WT PSI (51 ms and 211 ms).

TABLE 2

Fitting coefficients of $P_{700}^{+}$ decay in purified PSI under anoxia

| Parameter | Sonication protocol $WT^{H6}$ | $\Psi H3^{H6}$-1 |
|---|---|---|
| $\tau_1$ (ms) | 24.3 ± 1.4 | 51.4 ± 2.5 |
| $A_1$ (%) | 48.9 ± 3.4 | 54.9 ± 2.9 |
| $\tau_2$ (ms) | 98.1 ± 5.7 | 210.7 ± 16.3 |
| $A_2$ (%) | 46.4 ± 3.4 | 31.8 ± 2.9 |
| $\tau_3$ (s) | 13.4 ± 5.5 | 11.0 ± 1.3 |
| $A_3$ (%) | 3.3 ± 0.5 | 9.7 ± 0.3 |
| $A_0$ (%) | 1.6 ± 0.6 | 3.6 ± 0.4 |
| $R^2$ | 0.99989 | 0.99986 |

Figure 11:
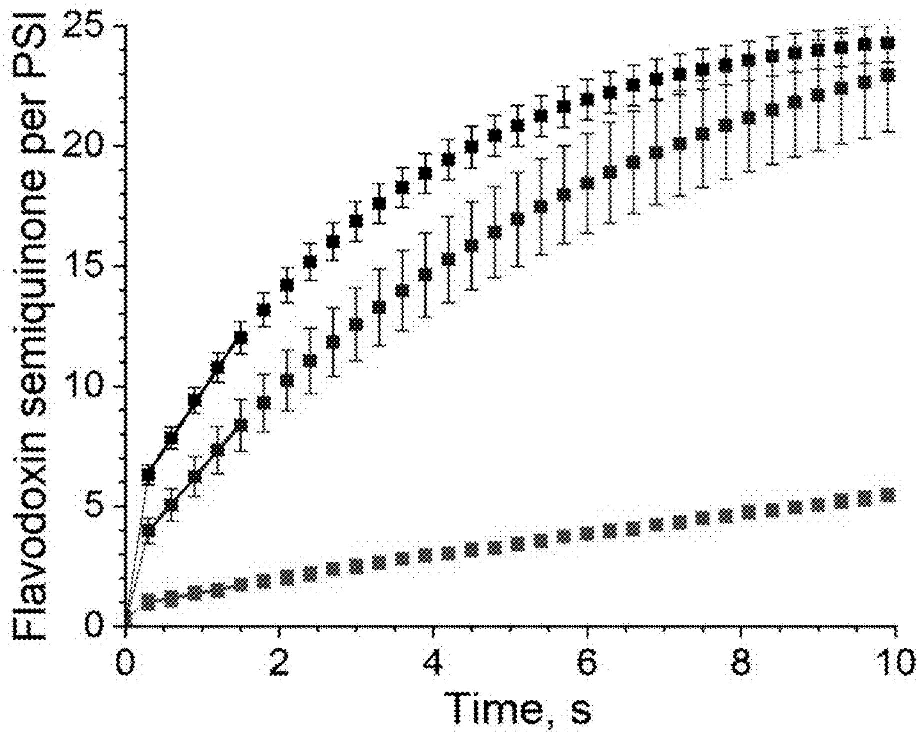
FIG. 11 presents flavodoxin photoreduction by PSI in vitro under saturating (3000 μmol $m^{-2}$ $s^{-1}$ PAR (photosynthetically active radiation, red light) illumination. Flavodoxin is ~50 fold excess of PSI (black=JVD-$1b^{-H6}$, blue=$WT^{H6}$ and red=$ΨH3^{H6}$). Turnover rates (derived from a linear fit as shown in bold line) are 5.7±0.3 Flvd $s^{-1}$ $(PSI)^{-1}$, 4.4±0.6 Flvd $s^{-1}$ $(PSI)^{-1}$ and 0.7±0.1 Flvd $s^{-1}$ $(PSI)^{-1}$ for WT-PSI: JVD-$1b^{-H6}$, $WT^{H6}$, and PSI-MeHydA respectively. Error bars represent standard error (n=3).

In vitro activity toward flavodoxin photoreduction: An ideal PSI-HydA chimera would direct all electrons to the hydrogenase domain. In such a situation, the rate of reduction of its normal electron acceptor would approach zero. To test the ability of PSI-MeHydA to reduce cyanobacterial flavodoxin, purified PSI or PSI-MeHydA complexes (~0.1 μM), reduced plastocyanin (50-fold excess) and ascorbate (5 mM) were used as electron donors, under anoxia with a ~50-fold excess of flavodoxin exposed to brief illuminations of saturating actinic light. The linear rate determined over a ~1 s interval (FIG. 11) is ~15.9±2.4% that of $WT^{H6}$ and 12.3±2.4% relative to JVD-$1b^{H6}$ PSI. Thus, the addition of the MeHydA domain to PsaC lowers flavodoxin reduction by a factor of 6-8.

Direct reduction of flavodoxin (or ferredoxin) by PSI-MeHydA in vitro could be viewed as a reciprocal function of proton reduction activity by the chimeric complex since the 2 processes are in competition when the hydrogenase active site is functional. Flavodoxin and ferredoxin share the binding interface on PSI, which requires the collaboration of PsaC, PsaD and PsaE forming a stromal ridge[41]. Moreover, PSI lacking the $F_B$ cluster show no flavodoxin reduction from the remaining FA cluster of PsaC[42]. The PSI-HydA2 and PSI-HydA1 chimeras exhibit flavodoxin reduction in the presence of $O_2$, hence, the rates for the semiquinone formation by WT PSI are an order of magnitude lower than are shown here, despite similar setup. Under oxic conditions and with a large excess of flavodoxin relative to PSI, competing processes of flavodoxin semiquinone reoxidation by $O_2$ take place and usually no significant accumulation of flavodoxin hydroquinone occurs[43]. For that reason, only the initial 4 points were used to determine steady-state rate of flavodoxin reduction. Thusly, 6-8 times drop in flavodoxin steady-state photoreduction rate (per PSI complex) by PSI-MeHydA is comparable to previously made constructs. This suggests that flavodoxin “binding” does not involve interaction with hydrogenase domain of the chimeric complex and perhaps is limited to PsaC domain and linking regions. It is important to remember that this in vitro experiment is not representative of what is occurring in vivo, as the hydrogenase active site is damaged during purification of the PSI-HydA chimera—thus, there is no competition with proton reduction.

Figure 16:
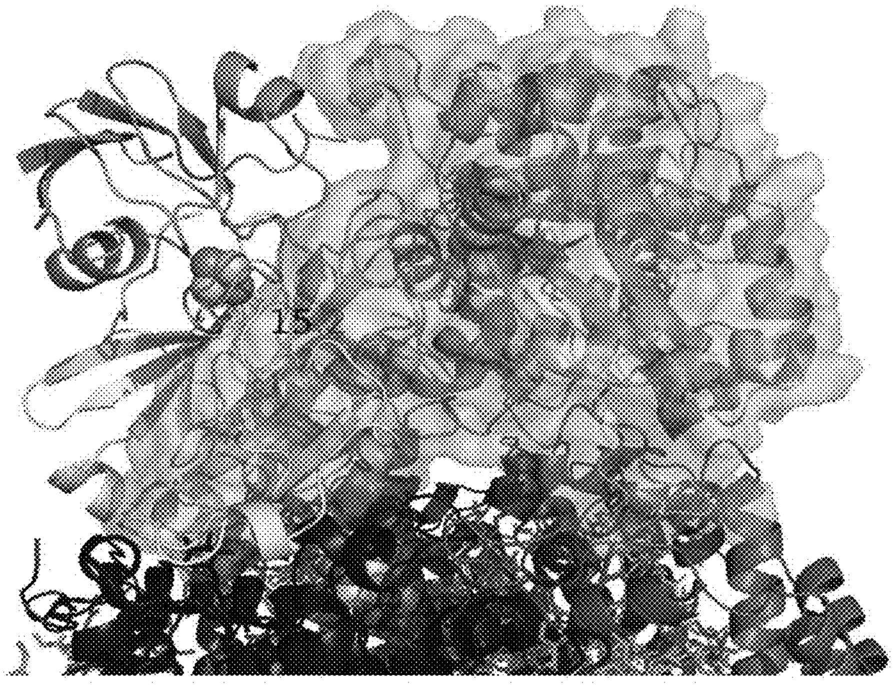
FIG. 16 presents a model of Ferredoxin Fd1 docking to PSI-MeHydA. Subunits of the chimeric PSI are PsaC-MeHydA (cyan), PsaA (red), PsaB (blue), PsaD (yellow) and PsaF (magenta) with Chl shown as green sticks. Fd shown as orange cartoon. Edge-to-edge distance between [2Fe-2S] cluster of Fd and $F_B$ is 15.2 Å.

To find a probable site for Fd binding on PSI-MeHydA, the generated PsaC-MeHydA with PsaA, PsaB, PsaD, and PsaF subunits was used as a receptor for Fd hard docking as previously described[18]. With a single distant restraint between C14 ($F_B$) and outermost C42 of Fd (limited to 20 Å), the most likely docking model places Fd in a different position than typical WT ferredoxin site (FIG. 16). The distance between ferredoxin [2Fe-2S] cluster and $F_B$ is ~15.2 Å and is larger than the docked model of Fd with PSI-HydA1. Polar interactions with MeHydA domain play a significant role in the proposed model (see Table 3 below) but overall has less significant pairs than PSI-HydA1-Fd model.

TABLE 3

Important pairs of residues involved in Fd1 docking to PSI-MeHydA (FIG. 16).

| Ferredoxin 1 residue | PsaC-MeHydA residue | Distance (in Å) |
|---|---|---|
| S43 | G32 | 2.6 |
| Y94 | G33 | 2.5 |
| Y94 | L359 | 2.4 |
| | PsaD residue | |
| H88 | A163 | 3.2 |

Figures 12A, 12B, 12C, 12D:
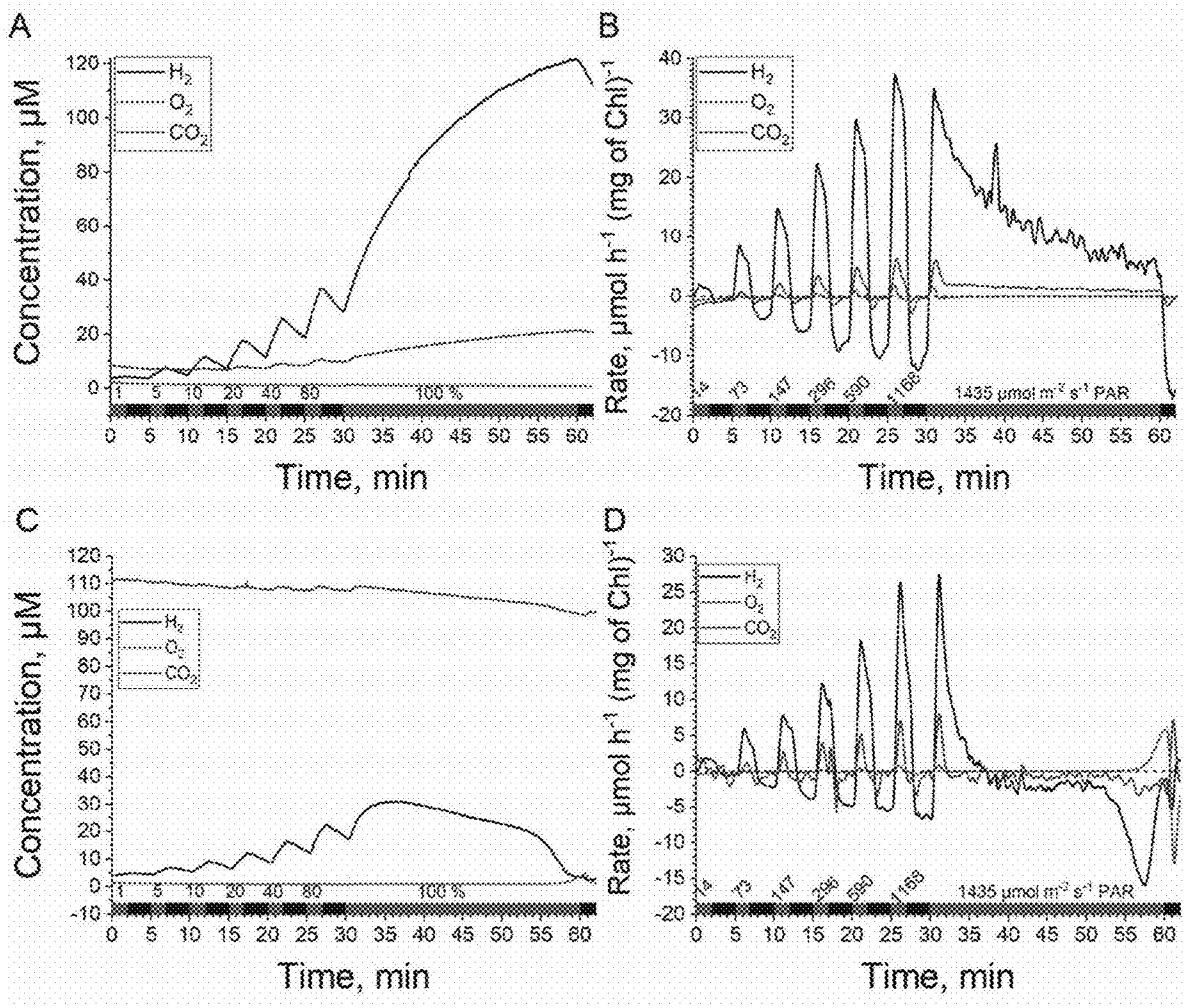
FIGS. 12A-12D present in vivo photosynthetic activity of $ΨH3^{H6}$ strain. $H_2$ (black), $O_2$ (red) and $CO_2$ (blue) concentrations (A, C) and the derivatives of their concentrations (B, D) in cultures of $ΨH3^{H6}$ cells resuspended in TP without added carbon source (A, B) or with 2 mM bicarbonate (C, D). Dotted line in B and D indicates zero rate. A single trial is reported.

In vivo photosynthetic activity of $\Psi H3^{H6}$ strain: When analyzing hydrogen production/oxidation activity of the $\Psi H3^{H6}$ strain, it is important to keep in mind that it has 3 hydrogenases enzymes: two endogenous enzymes (HydA1 and HydA2) and the chimeric PSI-MeHydA. This mutant’s ability to produce $H_2$ without added bicarbonate or acetate on a relatively short time scale was examined using MIMS (FIGS. 12A and B). The experiment consisted of 2 parts: a light-saturation portion (2 min light ON followed by 3 min OFF) and continuous maximal light portion. During the light-saturation portion, the $H_2$ rate plateaued at ~1170 μE $m^{-2}$ $s^{-1}$ PAR with ~37 μmol $H_2$ $h^{-1}$ (mg $Chl)^{-1}$. On continuous light, the $H_2$ rate gradually dropped down to ~5 μmol $H_2$ $h^{-1}$ (mg $Chl)^{-1}$ as the dissolved $H_2$ concentration approached 120 μM. Just after the light was switched off, a maximal $H_2$ uptake rate of ~-17 μmol $H_2$ $h^{-1}$ (mg $Chl)^{-1}$ was observed. The $O_2$ concentration remained low throughout the experiment with small spikes appearing during dark-to-light transitions. The net $O_2$ production rate saturated with light, reaching its maximal value of ~2 μmol $O_2$ $h^{-1}$ (mg $Chl)^{-1}$ at 100% light intensity. The $CO_2$ concentration started at ~9 μM at the beginning of the experiment and more than doubled at the end of the continuous illumination portion. The $CO_2$ production rate coincided with $O_2$ spikes and saturated at maximal light intensity with the value of 6.3 μmol $CO_2$ $h^{-1}$ (mg $Chl)^{-1}$. No net $CO_2$ uptake was detected during illumination of cells.

Photobiological $H_2$ production of the $\Psi H3^{H6}$ strain on a short time scale had a maximal rate of 37 μmol $h^{-1}$ (mg $Chl)^{-1}$, as measured by MIMS. Using the ratio of 3420 Chl per $P_{700}$ determined for strain $\Psi H3^{H6}$-1, this would correspond to a turnover rate of ~31$H_2$ $s^{-1}$, assuming that each PSI-MeHydA complex is active. This number is comparable to the rate obtained for PSI-HydA2 in the ΨH1 strain—~52$H_2$ $s^{-1}$. The PSI-MeHydA turnover rate is about twice as high as PSI-HydA1 (16$H_2$ $s^{-1}$). A reciprocal relation of turnover number vs accumulation level of the PSI-HydA chimera may indicate that inactivation of the hydrogenase domain occurs faster and to a greater degree in a higher accumulating chimera.

When bicarbonate was added to the cells at the beginning of the experiment (FIGS. 12 C and D), there was about 2 times less $H_2$ produced in the light saturation portion and the maximal $H_2$ concentration was ~3 times less overall in comparison to the trial in which no bicarbonate was added. The $H_2$ rate saturated with light at the highest intensity tested (1.4 mmol photons $m^2$ $s^{-1}$), reaching 27 μmol $H_2$ $h^{-1}$ (mg Chl)$^{-1}$. In the continuous-illumination portion, the $H_2$ production rate dropped and became negative within 5 minutes of the onset. Towards the end of the illumination phase, the $H_2$ uptake rate suddenly accelerated, reaching ~15 μmol $H_2$ $h^{-1}$ (mg Chl)$^{-1}$, resulting in complete consumption of $H_2$. The $O_2$ concentration stayed low and only started significantly increasing once all $H_2$ was consumed. Spikes of transient $O_2$ production were observed at each dark-light transition, but were low (~1 μmol $O_2$ $h^{-1}$ (mg Chl)$^{-1}$ at the highest light intensity). When $H_2$ was exhausted towards the end of the illumination, the $O_2$ production rate rose to 6 μmol $O_2$ $h^{-1}$ (mg Chl)$^{-1}$ before the lights were turned off. Spikes of $CO_2$ production were also observed after each light-dark transition, saturating at 8 μmol $CO_2$ $h^{-1}$ (mg Chl)$^{-1}$ under maximal illumination. During continuous illumination, the $CO_2$ rate followed the $H_2$ rate, transitioning to $CO_2$ uptake 2 min after maximal illumination commenced.

The reduction in net $H_2$ production rate upon bicarbonate addition indicates the likely involvement of endogenous hydrogenases in concomitant $H_2/CO_2$ uptake processes competing with $H_2$ evolution processes by PSI-MeHydA. The $H_2/CO_2$ uptake eventually wins over as the CBB cycle activates, creating a large electron since, until $H_2$ is completely consumed and $O_2$ starts to build up (FIG. 12C). This creates an electron transport chain: PSI-MeHydA→$H_2$→HydA1/2→ferredoxin→NADPH→carbon fixation. This system has potential for directed evolution system of a more $O_2$ resistant hydrogenase in vivo. Assuming that $O_2$ inactivation of chimeric PSI-MeHydA is 10 times slower than algal endogenous hydrogenases, there should be available electrons from photosynthesis to drive $H_2/CO_2$ uptake by endogenous hydrogenases. Thus, by slowly allowing steady-state $O_2$ levels to rise in a photobioreactor setting, it may be possible to select mutants with more $O_2$-tolerant hydrogenases over many generations.

Figures 13A, 13B:
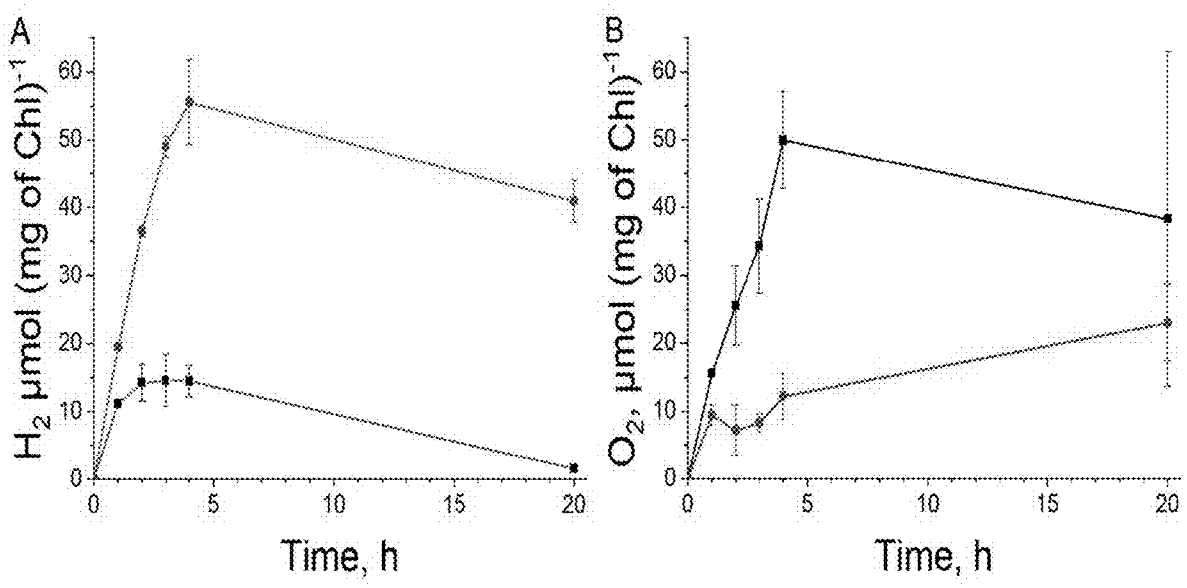
FIGS. 13A-13B present in vivo photosynthetic activity of $ΨH3^{H6}$ strain. Net headspace $H_2$ (A) and $O_2$ (B) produced by $ΨH3^{H6}$ (red) or $WT^{H6}$ (black) resuspended in TAP after 2 h anaerobic adaptation in the dark followed up by ~200 μmol $m^{-2}$ $s^{-1}$ PAR emitted by white LEDs. The sealed bottles were constantly agitated (except for headspace withdrawal). Error bars represent standard error (n=3).

Next, $H_2$ production was assessed on a longer scale. A sealed bottle experiment was set up with anaerobically adapted cultures and the headspace was periodically probed using GC (FIG. 13). Cells were resuspended with acetate-containing media to increase respiration and thereby protect hydrogenase from rapid inactivation. A significant difference in $H_2$ production by the $\Psi H3^{H6}$ strain in comparison to the $WT^{H6}$ control was observed. The initial $H_2$ production rate for $\Psi H3^{H6}$ was 19.5±0.6 μmol $H_2$ $h^{-1}$ (mg Chl)$^{-1}$ and remained quasi-linear for 3 hours at ~16 μmol $H_2$ $h^{-1}$ (mg Chl)$^{-1}$. After overnight illumination, headspace $H_2$ had decreased, presumably due to uptake. The initial $H_2$ production rate of the $WT^{H6}$ control was ~2-fold lower (11±0.1 μmol $H_2$ $h^{-1}$ (mg Chl)$^{-1}$) and rapidly declined, with headspace $H_2$ plateauing for the next 3 hours. (FIG. 13A) Thus, the $\Psi H3^{H6}$ culture produced roughly 4 times more $H_2$ than the $WT^{H6}$ control culture during a 4-h illumination period under these conditions.

Net $O_2$ was initially evolved at 9.5±1.5 μmol $O_2$ $h^{-1}$ (mg Chl)$^{-1}$ by $\Psi H3^{H6}$ for the first hour and then remained fairly stable at about 0.05% for the next 3 h. The amount of $O_2$ doubled overnight. In contrast, $WT^{H6}$ exhibited a linear rate of $O_2$ evolution in the first 4 hours at an average rate of 10.7 μmol $O_2$ $h^{-1}$ (mg Chl)$^{-1}$; $O_2$ reached 0.2% in the headspace and did not significantly change overnight. (FIG. 13B)

Figure 14:
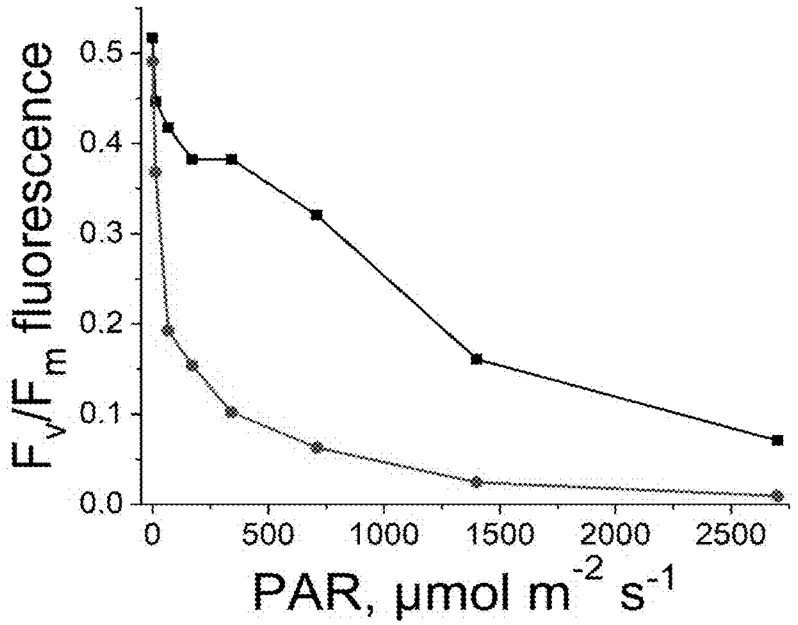
FIG. 14 presents chlorophyll (Chl) fluorescence of Photosystem II. $F_v/F_m$ of PSII for $WT^{H6}$ (black/square) and $\Psi H3^{H6}$ (red/circle). Cells were resuspended in sodium phosphate buffer (pH 7.0) containing 20% Ficoll and 2 mM sodium bicarbonate, and dark adapted for 5 min prior to measurements. Aerobic conditions were maintained by brief sparging with air.

It was also of interest to know how the $\Psi H3^{H6}$ strain would perform under fully aerobic conditions, as it must initially be grown this way. Chl fluorescence of Photosystem II was used to characterize its photosynthetic capacity for linear electron flow. $\Psi H3^{H6}$ strain saturates with relatively low light: at 67 μmol $m^{-2}$ $s^{-1}$ PAR (green LED at 520 nm) the quantum yield of PSII drops below 0.2. It takes almost 1500 μmol $m^{-2}$ $s^{-1}$ PAR for the $WT^{H6}$ control for a comparable decrease in quantum yield (FIG. 14).

Figure 15:
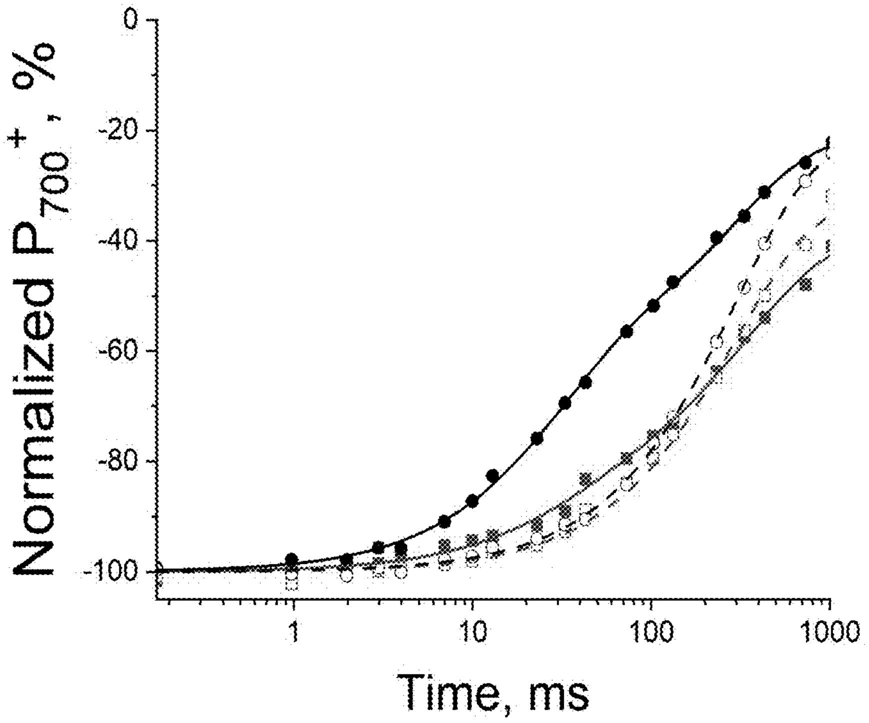
FIG. 15 presents $P_{700}$ dark recovery kinetics in $WT^{H6}$ (black) and $\Psi H3^{H6}$ (red) cells after 10 s of illumination with red light (~630 nm) at a flux of ~500 photons $PSI^{-1}$ $s^{-1}$. Cells were grown in TAP under low light before being resuspended in phosphate bicarbonate buffer, followed by addition of 10 μM DCMU (see Methods). Averages of $P_{700}^{+}$ reduction kinetics (n=5) in cells with DCMU (solid symbols) were fit to a biexponential decay (solid lines). Addition of 20 μM DBMIB to the same cells is indicated by hollow symbols; these transients were fit to a mono-exponential decay (dashed lines).

PSII activity was blocked with 3-(3,4-dichlorophenyl)-1,1-dimethylurea (DCMU) and the rate of $P_{700}^+$ decay was measured to estimate CEF around PSI (FIG. 15). CEF was ~2.2 times lower in $\Psi H3^{H6}$ chimeric strain (~3 $e^-$ $PSI^{-1}$ $s^{-1}$) compared to $WT^{H6}$. Addition of the cytochrome $b_6f$ inhibitor 2,5-dibromo-6-isopropyl-3-methyl-1,4-benzoquinone (DBMIB) resulted in the rate of $P_{700}^+$ re-reduction dropping >6-fold for the $WT^{H6}$ strain and 2-fold for $\Psi H3^{H6}$, approaching 1 $e^-$ $PSI^{-1}$ $s^{-1}$ for both.

$\Psi H3^{H6}$ doesn't show the same linearity to $O_2$ production and that could be due to increased mitochondrial respiration needed to compensate for the significantly reduced CEF in $\Psi H3^{H6}$ (FIG. 15). This is in line with previous findings on the pgr5 mutant lacking CEF[9]. Another likely case for decreased $O_2$ evolution by $\Psi H3^{H6}$ is inactivation of PSI-MeHydA by $O_2$. That would turn the chimeric protein into a bottleneck for electron transport chain as evidenced by PSII Chl fluorescence even at low light intensities (FIG. 14).

REFERENCES

[1] Hohmann-Marriott M F, Blankenship R E. Evolution of Photosynthesis. Annu Rev Plant Biol 2011; 62:515-48. https://doi.org/10.1146/annurev-arplant-042110-103811.

[2] Nelson N, Ben-Shem A. The complex architecture of oxygenic photosynthesis. Nat Rev Mol Cell Biol 2004; 5:971.

[3] Nelson N, Junge W. Structure and Energy Transfer in Photosystems of Oxygenic Photosynthesis. Annu Rev Biochem 2015; 84:659-83. https://doi.org/10.1146/annurev-biochem-092914-041942.

[4] Nawrocki W J, Bailleul B, Picot D, Cardol P, Rappaport F, Wollman F-A, et al. The mechanism of cyclic electron flow. Biochim Biophys Acta—Bioenerg 2019; 1860:433-8. https://doi.org/10.1016/j.bbabio.2018.12.005.

[5] Milrad Y, Schweitzer S, Feldman Y, Yacoby I. Green Algal Hydrogenase Activity Is Outcompeted by Carbon Fixation before Inactivation by Oxygen Takes Place. Plant Physiol 2018; 177:918-26. https://doi.org/10.1104/pp. 18.00229.

[6] Pinto T S, Malcata F X, Arrabaça J D, Silva J M, Spreitzer R J, Esquivel M G. Rubisco mutants of *Chlamydomonas reinhardtii* enhance photosynthetic hydrogen production. Appl Microbiol Biotechnol 2013; 97:5635-43. https://doi.org/10.1007/s00253-013-4920-z.

[7] Sun Y, Chen M, Yang H, Zhang J, Kuang T, Huang F. Enhanced H2 photoproduction by down-regulation of ferredoxin-NADP+ reductase (FNR) in the green alga *Chlamydomonas reinhardtii*. Int J Hydrogen Energy 2013; 38:16029-37. https://doi.org/10.1016/J.IJHYDENE.2013.10.011.

[8] Dang K-V, Plet J, Tolleter D, Jokel M, Cuiné S, Carrier P, et al. Combined Increases in Mitochondrial Cooperation and Oxygen Photoreduction Compensate for Deficiency in Cyclic Electron Flow in *Chlamydomonas reinhardtii*. Plant Cell 2014; 26:3036-50. https://doi.org/10.1105/tpc.114.126375.

[9] Elman T, Hoai Ho T T, Milrad Y, Hippler M, Yacoby I. Enhanced chloroplast-mitochondria crosstalk promotes ambient algal-H2 production. Cell Reports Phys Sci 2022; 3:100828. https://doi.org/10.1016/j.xcrp.2022.100828.

[10] Kozuleva M, Petrova A, Milrad Y, Semenov A, Ivanov B, Redding K E, et al. Phylloquinone is the principal Mehler reaction site within photosystem I in high light. Plant Physiol 2021; 186:1848-58. https://doi.org/10.1093/plphys/kiab221.

[11] Chaux F, Burlacot A, Mekhalfi M, Auroy P, Blangy S, Richaud P, et al. Flavodiiron Proteins Promote Fast and Transient O2 Photoreduction in *Chlamydomonas*. Plant Physiol 2017; 174:1825 LP-1836. https://doi.org/10.1104/pp. 17.00421.

[12] Lubitz W, Ogata H, Rüdiger O, Reijerse E. Hydrogenases. Chem Rev 2014; 114:4081-148. https://doi.org/10.1021/cr4005814.

[13] Engelbrecht V, Liedtke K, Rutz A, Yadav S, Gunzel A, Happe T. One isoform for one task? The second hydrogenase of *Chlamydomonas reinhardtii* prefers hydrogen uptake. Int J Hydrogen Energy 2021; 46:7165-75. https://doi.org/10.1016/j.ijhydene.2020.11.231.

[14] Eroglu E, Melis A. Microalgal hydrogen production research. Int J Hydrogen Energy 2016; 41:12772-98. https://doi.org/https://doi.org/10.1016/j.ijhydene.2016.05.115.

[15] Cournac L, Mus F, Bernard L, Guedeney G, Vignais P M, Peltier G. Limiting steps of hydrogen production in *Chlamydomonas reinhardtii* and Synechocystis PCC 6803 as analysed by light-induced gas exchange transients. Int J Hydrogen Energy 2002; 27:1229-37. https://doi.org/10.1016/S0360-3199(02)00105-2.

[16] Milrad Y, Schweitzer S, Feldman Y, Yacoby I. Bi-directional electron transfer between H2 and NADPH mitigates light fluctuation responses in green algae. Plant Physiol 2021; 186:168-79. https://doi.org/10.1093/plphys/kiab051.

[17] Kanygin A, Milrad Y, Thummala C, Reifschneider K, Baker P, Marco P, et al. Rewiring photosynthesis: a photosystem I-hydrogenase chimera that makes H2 in vivo. Energy Environ Sci 2020; 13:2903-14. https://doi.org/10.1039/C9EE03859K.

[18] Kanygin A, Smith A, Nagy V, Tóth S Z, Redding K E. Interplay between Hydrogen Production and Photosynthesis in a Green Alga Expressing an Active Photosystem I-hydrogenase Chimera. Int J Hydrogen Energy 2022; (accepted for publication on Mar. 11, 2022)

[19] Swanson K D, Ratzloff M W, Mulder D W, Artz J H, Ghose S, Hoffman A, et al. [FeFe]-Hydrogenase Oxygen Inactivation Is Initiated at the H Cluster 2Fe Subcluster. J Am Chem Soc 2015; 137:1809-16. https://doi.org/10.1021/ja510169s.

[20] Ghirardi M L, Togasaki R K, Seibert M. Oxygen sensitivity of algal H2-production. Appl Biochem Biotechnol 1997; 67:182. https://doi.org/10.1007/BF02787851.

[21] Nagy V, Podmaniczki A, Vidal-Meireles A, Tengölics R, Kovács L, Rákhely G, et al. Water-splitting-based, sustainable and efficient H2 production in green algae as achieved by substrate limitation of the Calvin-Benson-Bassham cycle. Biotechnol Biofuels 2018; 11:69. https://doi.org/10.1186/s13068-018-1069-0.

[22] Torzillo G, Scoma A, Faraloni C, Giannelli L. Advances in the biotechnology of hydrogen production with the microalga *Chlamydomonas reinhardtii*. Crit Rev Biotechnol 2015; 35:485-96. https://doi.org/10.3109/07388551.2014.900734.

[23] Redding K E, Appel J, Boehm M, Schuhmann W, Nowaczyk M M, Yacoby I, et al. Advances and challenges in photosynthetic hydrogen production. Trends Biotechnol 2022. https://doi.org/10.1016/j.tibtech.2022.04.007.

[24] Hwang J-H, Lee W H. Continuous photosynthetic biohydrogen production from acetate-rich wastewater: Influence of light intensity. Int J Hydrogen Energy 2021; 46:21812-21. https://doi.org/10.1016/j.ijhydene.2021.04.052.

[25] Atta M, Meyer J. Characterization of the gene encoding the [Fe]-hydrogenase from *Megasphaera elsdenii*. Biochim Biophys Acta—Protein Struct Mol Enzymol 2000; 1476:368-71. https://doi.org/10.1016/50167-4838(99)00245-9.

[26] Sievers F, Wilm A, Dineen D, Gibson T J, Karplus K, Li W, et al. Fast, scalable generation of high-quality protein multiple sequence alignments using Clustal Omega. Mol Syst Biol 2011; 7:539. https://doi.org/10.1038/msb.2011.75.

[27] Kelley L A, Mezulis S, Yates C M, Wass M N, Sternberg M J E. The Phyre2 web portal for protein modeling, prediction and analysis. Nat Protoc 2015; 10:845-58. https://doi.org/10.1038/nprot.2015.053.

[28] Schrödinger L. The {PyMOL} Molecular Graphics System, Version 2.4.0. 2015.

[29] Suga M, Ozawa S-I, Yoshida-Motomura K, Akita F, Miyazaki N, Takahashi Y. Structure of the green algal photosystem I supercomplex with a decameric light-harvesting complex I. Nat Plants 2019; 5:626-36. https://doi.org/10.1038/s41477-019-0438-4.

[30] Kozakov D, Hall D R, Xia B, Porter K A, Padhorny D, Yueh C, et al. The ClusPro web server for protein-protein docking. Nat Protoc 2017; 12:255. https://doi.org/10.1038/nprot.2016.169.

[31] Song Y, DiMaio F, Wang R Y-R, Kim D, Miles C, Brunette T, et al. High-Resolution Comparative Modeling with Rosetta C M. Structure 2013; 21:1735-42. https://doi.org/10.1016/j.str.2013.08.005.

[32] Fischer N, Sétif P, Rochaix J D. Targeted Mutations in the psaC Gene of *Chlamydomonas reinhardtii*: Preferential Reduction of FB at Low Temperature Is Not Accompanied by Altered Electron Flow from Photosystem I to Ferredoxin. Biochemistry 1997; 36:93-102. https://doi.org/10.1021/bi962244v.

[33] Gulis G, Narasimhulu K V, Fox L N, Redding K E. Purification of His6-tagged Photosystem I from *Chlamydomonas reinhardtii*. Photosynth Res 2008; 96:51-60. https://doi.org/10.1007/s11120-007-9283-9.

[34] Kropat J, Hong-Hermesdorf A, Casero D, Ent P, Castruita M, Pellegrini M, et al. A revised mineral nutrient supplement increases biomass and growth rate in *Chlamydomonas reinhardtii*. Plant J 2011; 66:770-80. https://doi.org/10.1111/j.1365-313X.2011.04537.x.

[35] Porra R J, Thompson W A, Kriedemann P E. Determination of accurate extinction coefficients and simultaneous equations for assaying chlorophylls a and b extracted with four different solvents: verification of the concentration of chlorophyll standards by atomic absorption spectrosco. Biochim Biophys Acta—Bioenerg 1989; 975:384-94. https://doi.org/10.1016/S0005-2728(89)80347-0.

[36] Gerde J A, Montalbo-Lomboy M, Yao L, Grewell D, Wang T. Evaluation of microalgae cell disruption by ultrasonic treatment. Bioresour Technol 2012; 125:175-81. https://doi.org/10.1016/j.biortech.2012.08.110.

[37] Caserta G, Papini C, Adamska-Venkatesh A, Pecqueur L, Sommer C, Reijerse E, et al. Engineering an [FeFe]-Hydrogenase: Do Accessory Clusters Influence O 2 Resistance and Catalytic Bias? J Am Chem Soc 2018; 140:5516-26. https://doi.org/10.1021/jacs.8b01689.

[38] Brettel K. Electron transfer and arrangement of the redox cofactors in photosystem I. Biochim Biophys Acta—Bioenerg 1997; 1318:322-73. https://doi.org/10.1016/S0005-2728(96)00112-0.

[39] Sawyer A, Bai Y, Lu Y, Hemschemeier A, Happe T. Compartmentalisation of [FeFe]-hydrogenase maturation in *Chlamydomonas reinhardtii*. Plant J 2017; 90:1134-43. https://doi.org/10.1111/tpj.13535.

[40] Suslick K S. Sonochemistry. Science (80-) 1990; 247:1439-45. https://doi.org/10.1126/science.247.4949.1439.

[41] Sétif P. Ferredoxin and flavodoxin reduction by photosystem I. Biochim Biophys Acta—Bioenerg 2001; 1507:161-79. https://doi.org/https://doi.org/10.1016/50005-2728(01)00205-5.

[42] Vassiliev I R, Jung Y-S, Yang F, Golbeck J H. PsaC Subunit of Photosystem I Is Oriented with Iron-Sulfur Cluster FB as the Immediate Electron Donor to Ferredoxin and Flavodoxin. Biophys J 1998; 74:2029-35. https://doi.org/10.1016/S0006-3495(98)77909-3.

[43] Mühlenhoff U, Sétif P. Laser Flash Absorption Spectroscopy Study of Flavodoxin Reduction by Photosystem I in Synechococcus sp. PCC 7002. Biochemistry 1996; 35:1367-74. https://doi.org/10.1021/bi952381c.

[44] Reifschneider-Wegner et al. Expression of the [FeFe] hydrogenase in the chloroplast of *Chlamydomonas reinhardtii*. Int J of Hydrogen Energy 39: 3657-3665 (2014).

We claim:

1. A genetically engineered cell comprising a polynucleotide encoding a fusion protein comprising a photosystem I (PSI) protein PsaC and bacterial hydrogenase A (HydA), wherein the fusion protein comprises SEQ ID NO: 1 or 12.

2. The cell of claim 1, wherein the cell is an algal cell.

3. The cell of claim 2, wherein the cell is selected from *Chlamydomonas reinhardtii, Chlorella vulgaris, Picochlorum soloecismus, Galdieria sulphuraria* and *Cyanidioschyzon merolae.*

4. An algal biomass comprising the genetically engineered cell of claim 1.

* * * * *

SEQUENCE LISTING

```
Sequence total quantity: 18
SEQ ID NO: 1            moltype = AA  length = 474
FEATURE                 Location/Qualifiers
source                  1..474
                        mol_type = protein
                        organism = synthetic construct
REGION                  1..31
                        note = PsaC fragment
REGION                  429..474
                        note = PsaC fragment
REGION                  32..33
                        note = N-terminal junction
REGION                  34..41
                        note = HydA2 N-terminus linker
REGION                  414..428
                        note = C-terminal linker
SEQUENCE: 1
MAHIVKIYDT CIGCTQCVRA CPLDVLEMVP WGGATATDAV PNDVDKVKAA LKDPEKIVIF  60
QTAPAVRVGL GEAFGMDPGT FVEGKMVAAL RTLGADYVFD TDFGADLTIM EEATELLHRL  120
QSEEIPIPQF TSCCPAWVEF AETFYPDLLQ HLSSTKSPIS ILSPVIKTYF AQQKNIDPKK  180
IVNVCVTPCT AKKAEIRRPE LSASGLFWDE PEIRDTDICI TTRELAQWIQ DENIDFASLE  240
DSKFDKAFGE ASGGGRIFGN SGGVMEAAIR TAYHMFTGRP APKDFIPFEP VRGLQGVKKA  300
TVIFGHFVLH VAAISGLGNA RAFIDDLIKN DAFEDYSFIE VMACPGGCIG GGGQPKVKLP  360
QVKKVQEART ASIYKSDEET DIKASWQNPE IETLYEAFLD EPLSEMAEFT LHTHYSAGSG  420
GGGSGAGGAS QMASAPRTED CVGCKRCETA CPTDFLSVRV YLGSESTRSM GLSY        474

SEQ ID NO: 2            moltype = AA  length = 15
FEATURE                 Location/Qualifiers
source                  1..15
                        mol_type = protein
                        organism = synthetic construct
SEQUENCE: 2
HYSAGSGGGG SGAGG                                                   15

SEQ ID NO: 3            moltype = DNA  length = 23
FEATURE                 Location/Qualifiers
source                  1..23
                        mol_type = other DNA
                        organism = synthetic construct
SEQUENCE: 3
taatatggag atgacatatt tag                                          23

SEQ ID NO: 4            moltype = DNA  length = 20
FEATURE                 Location/Qualifiers
source                  1..20
                        mol_type = other DNA
                        organism = synthetic construct
SEQUENCE: 4
gatctcacca agatactccc                                              20

SEQ ID NO: 5            moltype = AA  length = 6
```

```
FEATURE                Location/Qualifiers
source                 1..6
                       mol_type = protein
                       organism = synthetic construct
SEQUENCE: 5
GGAIVE                                                           6

SEQ ID NO: 6           moltype = AA  length = 8
FEATURE                Location/Qualifiers
source                 1..8
                       mol_type = protein
                       organism = synthetic construct
SEQUENCE: 6
YFSDKSGG                                                         8

SEQ ID NO: 7           moltype = AA  length = 81
FEATURE                Location/Qualifiers
source                 1..81
                       mol_type = protein
                       organism = Chlamydomonas reinhardtii
SEQUENCE: 7
MAHIVKIYDT CIGCTQCVRA CPLDVLEMVP WDGCKASQMA SAPRTEDCVG CKRCETACPT  60
DFLSVRVYLG SESTRSMGLS Y                                          81

SEQ ID NO: 8           moltype = AA  length = 81
FEATURE                Location/Qualifiers
source                 1..81
                       mol_type = protein
                       organism = Chlorella vulgaris
SEQUENCE: 8
MSHTVKIYDT CIGCTQCVRA CPTDVLEMVP WDGCKASQIA SAPRTEDCVG CKRCESACPT  60
DFLSVRVYLG SETTRSMGLA Y                                          81

SEQ ID NO: 9           moltype = AA  length = 81
FEATURE                Location/Qualifiers
source                 1..81
                       mol_type = protein
                       organism = Picochlorum  soloecismus
SEQUENCE: 9
MSHTVKIYDT CIGCTQCVRA CPTDVLEMVP WNGCKANQIA SAPRTEDCVG CKRCESACPT  60
DFLSVRVYLG AETTRSMGLA Y                                          81

SEQ ID NO: 10          moltype = AA  length = 81
FEATURE                Location/Qualifiers
source                 1..81
                       mol_type = protein
                       organism = Cyanidioschyzon merolae
SEQUENCE: 10
MAHTVKIYDN CIGCTQCVRA CPLDVLEMVP WDGCKAGQMA SAPRTEDCVG CKRCETACPT  60
DFLSIRVYLG GETTRSMGLA Y                                          81

SEQ ID NO: 11          moltype = AA  length = 644
FEATURE                Location/Qualifiers
source                 1..644
                       mol_type = protein
                       organism = synthetic construct
SEQUENCE: 11
MGDNKKSFIQ SALGSVFSVF SEEELKELSN GRKIAICGKV NNPGIIEVPE GATLNEIIQL  60
CGGLINKSNF KAAQIGLPFG GFLTEDSLDK EFDFGIFYEN IARTIIVLSQ EDCIIQFEKF  120
YIEYLLAKIK DGSYKNYEVV KEDITEMFNI LNRISKGVSN MREIYLLRNL AVTVKSKMNQ  180
KHNIMEEIID KFYEEIEEHI EEKKCYTSQC NHLVKLTITK KCIGCGACKR ACPVDCINGE  240
LKKKHEIDYN RCTHCGACVS ACPVDAISAG DNTMLFLRDL ATPNKVVITQ MAPAVRVAIG  300
EAFGFEPGEN VEKKIAAGLR KLGVDYVFDT SWGADLTIME EAAELQERLE RHLAGDESVK  360
LPILTSCCPS WIKFIEQNYG DMLDVPSSAK SPMEMFAIVA KEIWAKEKGL SRDEVTSVAI  420
MPCIAKKYEA SRAEFSVDMN YDVDYVITTR ELIKIFENSG INLKEIEDEE IDTVMGEYTG  480
AGIIFGRTGG VIEAATRTAL EKMTGERFDN IEFEGLRGWD GFRVCELEAG DIKLRIGVAH  540
GLREAAKMLD KIRSGEEFFH AIEIMACVGG CIGGGGQPKT KGNKQAALQK RAEGLNNIDR  600
SKTLRRSNEN PEVLAIYEKY LDHPLSNKAH ELLHTVYFPR VKKD                  644

SEQ ID NO: 12          moltype = AA  length = 465
FEATURE                Location/Qualifiers
source                 1..465
                       mol_type = protein
                       organism = synthetic construct
REGION                 1..31
                       note = PsaC fragments
REGION                 420..465
                       note = PsaC fragments
REGION                 32..33
```

```
                        note = N-terminal junction
REGION                  34..41
                        note = HydA2 N-terminus linker
SEQUENCE: 12
MAHIVKIYDT CIGCTQCVRA CPLDVLEMVP WGGATATDAV PNTMLFLRDL ATPNKVVITQ  60
MAPAVRVAIG EAFGFEPGEN VEKKIAAGLR KLGVDYVFDT SWGADLTIME EAAELQERLE  120
RHLAGDESVK LPILTSCCPS WIKFIEQNYG DMLDVPSSAK SPMEMFAIVA KEIWAKEKGL  180
SRDEVTSVAI MPCIAKKYEA SRAEFSVDMN YDVDYVITTR ELIKIFENSG INLKEIEDEE  240
IDTVMGEYTG AGIIFGRTGG VIEAATRTAL EKMTGERFDN IEFEGLRGWD GFRVCELEAG  300
DIKLRIGVAH GLREAAKMLD KIRSGEEFFH AIEIMACVGG CIGGGGQPKT KGNKQAALQK  360
RAEGLNNIDR SKTLRRSNEN PEVLAIYEKY LDHPLSNKAH ELLHTVYFPR VKKDSGAGGA  420
SQMASAPRTE DCVGCKRCET ACPTDFLSVR VYLGSESTRS MGLSY                 465

SEQ ID NO: 13           moltype = AA  length = 484
FEATURE                 Location/Qualifiers
source                  1..484
                        mol_type = protein
                        organism = Megasphaera elsdenii
SEQUENCE: 13
MPEFHSRFEK IDRRVPIDEH NCAVQFDVTK CKNCTLCRRA CADTQTVLDY YSLSSTGDMP  60
ICVHCGQCSS ACPFGAIVEV NDVDKVKAAL KDPEKIVIFQ TAPAVRVGLG EAFGMDPGTF  120
VEGKMVAALR TLGADYVFDT DFGADLTIME EATELLHRLQ SEEIPIPQFT SCCPAWVEFA  180
ETFYPDLLQH LSSTKSPISI LSPVIKTYFA QQKNIDPKKI VNVCVTPCTA KKAEIRRPEL  240
SASGLFWDEP EIRDTDICIT TRELAQWIQD ENIDFASLED SKFDKAFGEA SGGGRIFGNS  300
GGVMEAAIRT AYHMFTGRPA PKDFIPFEPV RGLQGVKKAT VIFGHFVLHV AAISGLGNAR  360
AFIDDLIKND AFEDYSFIEV MACPGGCIGG GGQPKVKLPQ VKKVQEARTA SIYKSDEETD  420
IKASWQNPEI ETLYEAFLDE PLSEMAEFTL HTYFSDKSDQ LGRMKNLTPQ TNPMSPKYKP  480
PTEE                                                              484

SEQ ID NO: 14           moltype = AA  length = 441
FEATURE                 Location/Qualifiers
source                  1..441
                        mol_type = protein
                        organism = Chlamydomonas reinhardtii
SEQUENCE: 14
AAPAAEAPLS HVQQALAELA KPKDDPTRKH VCVQVAPAVR VAIAETLGLA PGATTPKQLA  60
EGLRRLGFDE VFDTLFGADL TIMEEGSELL HRLTEHLEAH PHSDEPLPMF TSCCPGWIAM  120
LEKSYPDLIP YVSSCKSPQM MLAAMVKSYL AEKKGIAPKD MVMVSIMPCT RKQSEADRDW  180
FCVDADPTLR QLDHVITTVE LGNIFKERGI NLAELPEGEW DNPMGVGSGA GVLFGTTGGV  240
MEAALRTAYE LFTGTPLPRL SLSEVRGMDG IKETNITMVP APGSKFEELL KHRAAARAEA  300
AAHGTPGPLA WDGGAGFTSE DGRGGITLRV AVANGLGNAK KLITKMQAGE AKYDFVEIMA  360
CPAGCVGGGG QPRSTDKAIT QKRQAALYNL DEKSTLRRSH ENPSIRELYD TYLGEPLGHK  420
AHELLHTHYV AGGVEEKDEK K                                           441

SEQ ID NO: 15           moltype = AA  length = 442
FEATURE                 Location/Qualifiers
source                  1..442
                        mol_type = protein
                        organism = Chlamydomonas reinhardtii
SEQUENCE: 15
TATDAVPHWK LALEELDKPK DGGRKVLIAQ VAPAVRVAIA ESFGLAPGAV SPGKLATGLR  60
ALGFDQVFDT LFAADLTIME EGTELLHRLK EHLEAHPHSD EPLPMFTSCC PGWVAMMEKS  120
YPELIPFVSS CKSPQMMMGA MVKTYLSEKQ GIPAKDIVMV SVMPCVRKQG EADREWFCVS  180
EPGVRDVDHV ITTAELGNIF KERGINLPEL PDSDWDQPLG LGSGAGVLFG TTGGVMEAAL  240
RTAYEIVTKE PLPRLNLSEV RGLDGIKEAS VTLVPAPGSK FAELVAERLA HKVEEAAAAE  300
AAAAVEGAVK PPIAYDGGQG FSTDDGKGGL KLRVAVANGL GNAKKLIGKM VSGEAKYDFV  360
EIMACPAGCV GGGGQPRSTD KQITQKRQAA LYDLDERNTL RRSHENEAVN QLYKEELGEP  420
LSHRAHELLH THYVPGGAEA DA                                          442

SEQ ID NO: 16           moltype = AA  length = 464
FEATURE                 Location/Qualifiers
source                  1..464
                        mol_type = protein
                        organism = synthetic construct
SEQUENCE: 16
MAHIVKITDT CIGCTQCVRA CPLDVLEMVP WGGAIVEVND VDKVKAALKD PEKIVIFQTA  60
PAVRVGLGEA FGMDPGTFVE GKMVAALRTL GADYVFDTDF GADLTIMEEA TELLHRLQSE  120
EIPIPQFTSC CPAWVEFAET FYPDLLQHLS STKSPISILS PVIKTYFAQQ KNIDPKKIVN  180
VCVTPCTAKK AEIRRPELSA SGLFWDEPEI RDTDICITTR ELAQWIQDEN IDFASLEDSL  240
FDKAFGEASG GGRIFGNSGG VMEAAIRTAY HMFTGRPAPK DFIPFEPVRG LQGVKKATVI  300
FGHFVLHVAA ISGLGNARAF IDDLIKNDAF EDYSFIEVMA CPGGCIGGGG QPKVKLPQVK  360
KVQEARTASI YKSDEETDIK ASWQNPEIET LYEAFLDEPL SEMAEFTLHT YFSDKSGGAS  420
QMASAPRTED CVGCKRCETA CPTDFLSVRV YLGSESTRSM GLSY                  464

SEQ ID NO: 17           moltype = AA  length = 517
FEATURE                 Location/Qualifiers
source                  1..517
                        mol_type = protein
                        organism = synthetic construct
```

-continued

```
SEQUENCE: 17
MAHIVKIYDT CIGCTQCVRA CPLDVLEMVP WGGATATDAV PHWKLALEEL DKPKDGGRKV  60
LIAQVAPAVR VAIAESFGLA PGAVSPGKLA TGLRALGFDQ VFDTLFAADL TIMEEGTELL 120
HRLKEHLEAH PHSDEPLPMF TSCCPGWVAM MEKSYPELIP FVSSCKSPQM MMGAMVKTYL 180
SEKQGIPAKD IVMVSVMPCV RKQGEADREW FCVSEPGVRD VDHVITTAEL GNIFKERGIN 240
LPELPDSDWD QPLGLGSGAG VLFGTTGGVM EAALRTAYEI VTKEPLPRLN LSEVRGLDGI 300
KEASVTLVPA PGSKFAELVA ERLAHKVEEA AAAEAAAAVE GAVKPPIAYD GGQGFSTDDG 360
KGGLKLRVAV ANGLGNAKKL IGKMVSGEAK YDFVEIMACP AGCVGGGGQP RSTDKQITQK 420
RQAALYDLDE RNTLRRSHEN EAVNQLYKEF LGEPLSHRAH ELLHTHYVPG GASQMASAPR 480
TEDCVGCKRC ETACPTDFLS VRVYLGSEST RSMGLSY                         517

SEQ ID NO: 18          moltype = AA  length = 510
FEATURE                Location/Qualifiers
source                 1..510
                       mol_type = protein
                       organism = synthetic construct
SEQUENCE: 18
MAHIVKIYDT CIGCTQCVRA CPLDVLEMVP WGGATATDAV PHVQQALAEL AKPKDDPTRK  60
HVCVQVAPAV RVAIAETLGL APGATTPKQL AEGLRRLGFD EVFDTLFGAD LTIMEEGSEL 120
LHRLTEHLEA HPHSDEPLPM FTSCCPGWIA MLEKSYPDLI PYVSSCKSPQ MMLAAMVKSY 180
LAEKKGIAPK DMVMVSIMPC TRKQSEADRD WFCVDADPTL RQLDHVITTV ELGNIFKERG 240
INLAELPEGE WDNPMGVGSG AGVLFGTTGG VMEAALRTAY ELFTGTPLPR LSLSEVRGMD 300
GIKETNITMV PAPGSKFEEL LKHRAAARAE AAAHGTPGPL AWDGGAGFTS EDGRGGITLR 360
VAVANGLGNA KKLITKMQAG EAKYDFVEIM ACPAGCVGGG GQPRSTDKAI TQKRQAALYN 420
LDEKSTLRRS HENPSIRELY DTYLGEPLGH KAHELLHTHY VAGGASQMAS APRTEDCVGC 480
KRCETACPTD FLSVRVYLGS ESTRSMGLSY                                 510
```